US008926999B2

(12) United States Patent  
Toreki et al.

(10) Patent No.: US 8,926,999 B2
(45) Date of Patent: Jan. 6, 2015

(54) ANTIMICROBIAL TEXTILES COMPRISING PEROXIDE

(75) Inventors: William Toreki, Gainesville, FL (US); Albina Mikhaylova, Gainesville, FL (US); Susan Leander, Gainesville, FL (US); Bernd Liesenfeld, Gainesville, FL (US); Gerald M. Olderman, Bedford, MA (US)

(73) Assignee: Quick-Med Technologies, Inc., Gainesville, FL (US)

( * ) Notice: Subject to any disclaimer, the term of this patent is extended or adjusted under 35 U.S.C. 154(b) by 0 days.

(21) Appl. No.: 13/616,209

(22) Filed: Sep. 14, 2012

(65) Prior Publication Data

US 2013/0011491 A1    Jan. 10, 2013

Related U.S. Application Data

(60) Division of application No. 12/971,659, filed on Dec. 17, 2010, now Pat. No. 8,277,827, which is a continuation-in-part of application No. PCT/US2010/037850, filed on Jun. 8, 2010.

(60) Provisional application No. 61/267,013, filed on Dec. 5, 2009, provisional application No. 61/184,931, filed on Jun. 8, 2009.

(51) Int. Cl.
```
A01N 59/00     (2006.01)
B05D 3/00      (2006.01)
A01P 1/00      (2006.01)
D06M 11/50     (2006.01)
C09K 3/00      (2006.01)
D06M 11/155    (2006.01)
D06M 11/65     (2006.01)
D06M 16/00     (2006.01)
```

(52) U.S. Cl.
CPC ............ D06M 11/50 (2013.01); D06M 11/155 (2013.01); D06M 11/65 (2013.01); D06M 16/00 (2013.01)
USPC ............... 424/411; 8/115.51; 252/182.33; 252/182.32; 252/182.34; 427/372.2; 427/385.5; 427/2.31; 427/240; 427/355

(58) Field of Classification Search
None
See application file for complete search history.

(56) References Cited

U.S. PATENT DOCUMENTS

| | | | |
|---|---|---|---|
| 2,791,518 A | 5/1957 | Stokes et al. | |
| 4,115,422 A | 9/1978 | Welch et al. | |
| 4,172,841 A | 10/1979 | Danna et al. | |
| 4,174,418 A | 11/1979 | Welch et al. | |
| 4,199,322 A | 4/1980 | Danna et al. | |
| 4,410,593 A | 10/1983 | Tomibe et al. | |
| 4,574,076 A | 3/1986 | Castrantas | |
| 4,892,905 A | 1/1990 | Lepert et al. | |
| 5,049,159 A | 9/1991 | Yamaji et al. | |
| 5,152,966 A | 10/1992 | Roe et al. | |
| 5,271,952 A | 12/1993 | Liang et al. | |
| 5,276,084 A | 1/1994 | Cheng et al. | |
| 5,458,906 A | 10/1995 | Liang | |
| 5,656,037 A | 8/1997 | Vigo et al. | |
| 5,882,357 A | 3/1999 | Sun et al. | |
| 5,919,507 A * | 7/1999 | Beelman et al. | 426/268 |
| 6,034,010 A | 3/2000 | Cartwright et al. | |
| 6,576,154 B1 | 6/2003 | Li | |
| 6,962,608 B1 | 11/2005 | Sun et al. | |
| 7,442,677 B1 | 10/2008 | Wagner | |
| 2003/0159200 A1 | 8/2003 | Elrod | |
| 2003/0162685 A1 * | 8/2003 | Man et al. | 510/445 |
| 2004/0266650 A1 * | 12/2004 | Lambotte et al. | 510/438 |
| 2005/0233920 A1 | 10/2005 | Stolte et al. | |
| 2006/0045899 A1 | 3/2006 | Sarangapani | |
| 2012/0064138 A1 * | 3/2012 | Beveridge et al. | 424/405 |

FOREIGN PATENT DOCUMENTS

| | | |
|---|---|---|
| CN | 1178232 | 4/1998 |
| JP | 2003026422 A | 1/2003 |
| WO | PCT/GB2009/001067 | 11/2010 |

OTHER PUBLICATIONS

Cahn et al. Liquid Detergents: An Overview. 2006 (e-book).
Yuan Gao and Robin Cranston. "Recent Advances in Antimicrobial Treatments of Textiles", Textile Research Journal vol. 78(1), p. 60-72 (2008).
Rosenthal-Toib, et al, "Synthesis of Stabilized Nanoparticles of Zinc Peroxide", Chemical Engineering Journal (136 (2008), p. 425-429.
Tim Padgett, "Is Drywall the Next Chinese Import Scandal?" Time, Mar. 23, 2009.
Mairin B. Brennan, "Knitting Textile Chemistry to Medicine", Chem. Eng. News, 1999, 77(36) p. 33-36.
US 5,872,068, 02/1999, Cartwright et al. (withdrawn).

* cited by examiner

*Primary Examiner* — David J Blanchard
*Assistant Examiner* — Sarah Alawadi
(74) *Attorney, Agent, or Firm* — Gerry J. Elman; Elman Technology Law, P.C.

(57) ABSTRACT

This invention pertains to method for imparting a durable antimicrobial activity to substrates, particularly textiles. An acetate-free metal and peroxide antimicrobial treatment formulation is prepared from a metal derivative, hydrogen peroxide and a source of hydroxide ion. The substrate is treated with the composition and dried to afford the treated substrate with antimicrobial activity. Zinc salts, ions, or complexes are preferred.

31 Claims, 1 Drawing Sheet

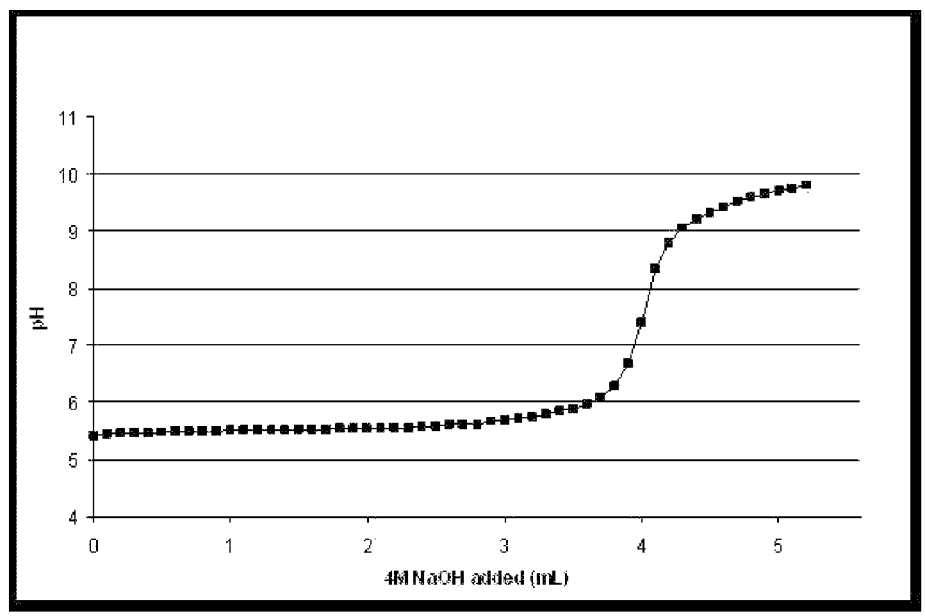
Plot of pH versus amount of hydroxide added to a mixture of 1.00 gram zinc chloride, 5.7 grams of Hydrogen Peroxide (35%), and 93.3 grams of water.

ANTIMICROBIAL TEXTILES COMPRISING PEROXIDE

CROSS-REFERENCE TO RELATED APPLICATIONS

This application is a Divisional of our U.S. application Ser. No. 12/971,659 filed Dec. 17, 2010 and scheduled to issue Oct. 2, 2012 as U.S. Pat. No. 8,277,827, which is a Continuation-in-Part of, and claims benefit of International Patent Application, Serial Number PCT/US2010/037850 filed Jun. 8, 2010, which claims benefit of U.S. Provisional Patent Application 61/267,013 filed Dec. 5, 2009 and U.S. Provisional Patent Application 61/184,931 filed Jun. 8, 2009. The entire disclosures of each of the aforementioned applications are incorporated herein by reference.

TECHNICAL FIELD

This invention pertains to antimicrobial textiles with durable antimicrobial properties.

BACKGROUND ART

Antimicrobial agents are chemical compositions that are used to prevent microbiological contamination and deterioration of products, materials, and systems. Particular areas of application of antimicrobial agents and compositions are, for example, cosmetics, disinfectants, sanitizers, wood preservation, food, animal feed, cooling water, metalworking fluids, hospital and medical uses, plastics and resins, petroleum, pulp and paper, textiles, latex, adhesives, leather and hides, and paint slurries. A wide range of disinfectants is known, as discussed for example in Disinfection, Sterilization, and Preservation, edited and partially written by Professor Seymour S. Block, Fourth Edition, published 1991 by Lea & Febiger, Pennsylvania. Certain peroxygen compounds, chlorine compounds, phenolics, quaternary ammonium compounds and surface active agents are known for their germicidal properties. The rate of disinfection is relatively slow in many cases, and some compounds emit volatile organic compounds or leave a persistent residue in the environment.

There has been a great deal of attention in recent years given to the hazards of bacterial contamination from potential everyday exposure. Noteworthy examples of such concern include the fatal consequences of food poisoning due to certain strains of Escherichia coli (E. coli) being found within undercooked beef, especially in fast food restaurants; Salmonella contamination causing sicknesses from undercooked and unwashed poultry food products; and illnesses and skin infections attributed to Staphylococcus aureus, Klebsiella pneumoniae, yeast, and other unicellular organisms. With such an increased consumer interest in this area, manufacturers have begun introducing antimicrobial agents within various household products and articles. For instance, certain brands of polypropylene cutting boards and liquid soaps contain antimicrobial compounds. The most popular antimicrobial for such articles is triclosan. Although the incorporation of such a compound within liquid or polymeric media has been relatively simple, other substrates, including the surfaces of textiles and fibers, have proven less accessible.

There is a long-felt need to provide effective, durable, and long-lasting antimicrobial characteristics for textile surfaces, in particular on apparel fabrics, and on film surfaces. Such proposed applications have been extremely difficult to accomplish with triclosan, particularly when wash durability is a necessity, as triclosan easily washes off any such surfaces. Furthermore, although triclosan has proven effective as an antimicrobial, contact with the compound may cause skin irritation, which makes the use of triclosan with fibers, films, and textile fabrics for apparel uses undesirable.

Textile articles that have been treated to render them microbicidal to microorganisms coming in contact with the article are known in the prior art. Such articles include those made from paper, fibers, woven and non-woven textiles and like fabrics which are designed for use in environments such as hospitals, food processing plants, laboratories and other areas where maintenance of germ-free conditions is essential. A recent review of antimicrobially treated textiles is found in "Recent Advances in Antimicrobial Treatments of Textiles", Y. Gao and R. Cranston, TEXTILE RESEARCH JOURNAL Vol. 78(1), p 60-72 (2008).

Antimicrobial materials such as fabrics, fibers, polymers and even children's toys have become increasingly popular due to public concerns over epidemiological diseases and pathogens. With respect to antimicrobial fabrics, domestic and international markets have grown significantly as a result of public awareness of these potential threats (see, Center for Disease Control and Prevention, Infection Control and Biosafety, Medical Data International. Report #RP-701530, 1992; and A. J. Rigby, et al., Fiber Horizons, December 1993, p 42-460). Antimicrobial clothing can be used in medicine as well as other institutional uses for such applications as, surgeon's gowns, caps, masks, patient drapes, bandages, towels, linens, wipers and cover cloths of various sizes.

Although the demand for antimicrobial fibers is high, few of such fibers are available, especially ones that are effective against a broad spectrum of bacteria and, which are effective after multiple machine washes. Research and development of durable functional fibers has been active in recent years, with new methods of incorporating antibiotics as bactericidal agents into polymers being advanced.

Many types of antibacterial agents have been applied to fibrous substrates. However, there are very few agents that retain their germicidal activity after repeated laundering, pose no environmental problems, do not cause undesirable side effects to either the substrate or user thereof, and are inexpensive to manufacture.

For example, U.S. Pat. No. 2,791,518 discloses a method of imparting microbicidal properties to articles such as textiles by immersing the article in a first aqueous solution containing a water-soluble basic nitrogen compound (ammonia) and a monovalent silver salt soluble in said solution, followed by a second immersion in a second solution containing a second salt capable of ion exchange with the silver salt such that a monovalent silver salt precipitate is formed within the article. The formed silver precipitate is sparingly water soluble and imparts microbicidal properties to the articles so treated.

Similarly, U.S. Pat. No. 5,271,952 discloses a method of treating fibers to render them electrically conductive as well as anti-bacterial comprising immersing the fibers in a bath comprising an aqueous solution of a source of divalent copper ions, a reducing agent, sodium thiosulfate and a source of iodide ions, whereby copper iodide is adsorbed into the fibers. Similar techniques for rendering fibers conductive or resistant to bacteria involving the use of copper compounds are disclosed in U.S. Pat. Nos. 4,410,593 and 5,458,906.

It has also been disclosed that materials such as chlorinated hydantoins may be grafted to textiles for the purpose of imparting antimicrobial properties, (Williams et al, C&EN Sep. 6, 1999, page 36; also U.S. Pat. No. 6,576,154). However, textiles so treated tend to suffer severe diminishment of antimicrobial properties after as few as 5 hours of laundering and are UV unstable over long durations of exposure.

U.S. Pat. No. 5,882,357 discloses durable and regenerable cellulose materials by using a chemical finishing method. Cotton and polyester/cotton fabrics were finished by treatment with hydantoin derivatives, and biocidal properties were conferred by washing the treated fabrics with chlorine laundry bleach. Chlorination of amide and imide bonds in hydantoin rings produces biocidal N-halamine sites. The N-halamine return to their precursor forms when the sites are exposed to microorganisms. The biocidal properties of the fibers can then be regenerated by using chlorine bleach. The major advantages of this chlorine regenerable finishing method are its durability, convenience and economy. N-halamine chemistry, however, is not applicable to colorized fabrics. The use of chlorine bleach decolorizes fibers. Thus, a non-bleach regenerating agent would be desirable for certain applications, especially for colored materials.

Hydrogen peroxide is well known as a safe and effective topical disinfectant and antiseptic that is applied as a dilute aqueous solution to cleanse wounds. However, it has no substantivity to fibrous materials and is readily removed from fabrics or fibrous assemblies by a single wash.

Hydrogen peroxide is finding favor in many applications because its breakdown products, water and oxygen, are innocuous, and it tends to have broad spectrum antimicrobial activity. Hydrogen peroxide is effective against many species of bacteria, mold, fungi and viruses. Broad spectrum activity is important in situations where harmful organisms are present but their identity is not known. Hydrogen peroxide is a well known antiseptic that has been extensively employed in aqueous solution for the treatment of infectious processes in both human and veterinary topical therapy. The agent can be used in its original form after suitable dilution, or it can be derived from those solid compounds which form salts or additive compounds with hydrogen peroxide. Included among these are sodium perborate, sodium carbonate peroxide, sodium peroxyphosphate, urea peroxide, potassium persulfate, and others. When added to water, these compounds hydrolyze into hydrogen peroxide and the corresponding carrying salt. The principal limitations of commonly used peroxide aqueous solutions, however, are their poor shelf stability caused by the decomposition of hydrogen peroxide into gaseous oxygen and water at room temperature, and the transitory contact of the active oxygenating agent with the affected tissue. In addition, when such compositions are formed of additive compounds with hydrogen peroxide, it is common to prepare the adduct composition before incorporating it into the desired composition.

U.S. Pat. No. 6,962,608 discloses a process for preparing an antimicrobial fiber, said process comprising: (a) immersing a textile in an aqueous treating solution comprising an organic acid, wherein said organic acid has at least two carboxyl groups; and (b) treating said fiber with an oxidizing agent to produce a peroxycarboxylic acid function, thereby preparing an antimicrobial textile containing an average of 6 weight percent of the organic acid, which when not laundered at all demonstrated over 99% (2-log) reduction of *Escherichia coli*. This level of percentage reduction gradually decreased as the samples were subjected to additional washing, finally dropping to 85% (<1-log) after four washes.

U.S. Pat. Nos. 4,199,322 and 4,172,841, both to Danna et al., disclose applying solutions containing zinc acetate (ZA) or zinc acetate dihydrate and hydrogen peroxide (HP) to textiles, and then drying the treated textiles to obtain products with antimicrobial properties. Preferably, acetic acid is added to keep the solutions homogeneous (clear and without precipitate or solidification). The Danna references disclose that the solutions used to treat the textiles (the "aqueous reaction mixtures") "may contain 1% to 30% zinc acetate, and preferably from 1.5 to 10 moles of HP per mole of zinc acetate". In all cases, the formulations disclose in the Danna references use zinc acetate, $Zn(OAc)_2$, or zinc acetate dihydrate as the active agent. In other words, the Danna references teach that a 2:1 molar ratio of acetate to zinc must be used. The ratio of acetate to zinc is even higher if one considers that the Danna references also disclose there is a benefit to adding acetate in the form of acetic acid to the formulations. Even though the acetic acid produced as a reaction product between ZA and HP is removed (vaporized) during the drying step, the Danna references disclose that the reaction products "contain a significant proportion of acetyl groups". Any additional acetic acid intentionally added to the solution is likewise removed during the drying step. Excess HP is also vaporized during this step.

Danna et al., in U.S. Pat. No. 4,199,322 (column 2, line 63 to column 3, line 15) ("Danna '322"), discloses a description of the antimicrobial reaction product. The reaction product has the general structure shown in Formula I (below) wherein X ranges from 9 to 16, and Y ranges from 1 to 7. A simple calculation reveals that the ratio of acetate to zinc in the reaction product of the Danna '322 disclosure ranges from 2:10 (for the case where x=9 and y=1) to 2:23 (where x=16 and y=7). Therefore, there is generally a molar excess of 500% to over 1,000% zinc, relative to acetate in the reaction product. Or stated alternatively, there are only 1 to 2 acetate moieties per 10 zinc atoms in the final antimicrobial reaction product.

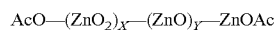

(X=9 to 16 and Y=1 to 7)  Formula 1

Since the initial ratio of acetate to zinc in the zinc acetate starting material is 2:1, this means that up to a 20-fold excess of acetate has been employed (not including any contribution from acetic acid that was intentionally added to the formulation). In other words, the reactants are rich in acetate, relative to zinc; whereas, the product is rich in zinc, relative to acetate. This excess acetate is removed as acetic acid during drying and is essentially wasted. This excessive consumption of reagent is costly from a materials standpoint, and it also poses other problems. The acid fumes are a health, safety, and environmental hazard. Acetic acid is flammable, with a flash point of approximately 40° C. In addition, the fumes are an irritation and respiratory hazard, and can be corrosive to equipment. Clearly, the methods described by Danna '322 have significant shortcomings.

Zinc acetate is freely soluble in water, and dissociates into zinc and acetate ions in solution. Using a 2:1 molar combination of sodium acetate and zinc chloride ($ZnCl_2$), instead of zinc acetate, would give essentially the same ratio of zinc and acetate ions in solution, and presumably achieve a similar antimicrobial effect.

Furthermore, the antimicrobial textiles produced by the methods of Danna '322 require a rinsing step in order to remove excess reaction products that cause the as-produced textiles to have the undesirable odor of acetic acid. Residual acetic acid can also be deleterious to the fabric itself, causing degradation or discoloration. Residual acetic acid may also pose health risks to the user of the treated textiles, such as skin irritation. It is also known that organic acids such as acetic acid can be utilized as a food source by certain microorganisms. The requirement for a rinsing step according to the process and methods of Danna '322 also adds significant cost to textile processing. The formulations of the Danna '322 must be dried prior to rinsing, in order to set (or fix, or cure)

the treatment. Subsequently rinsing the treated textile materials to remove acetic acid necessitates a second drying step, which adds significant energy cost.

Danna '322 discloses the use of a homogeneous solution which does not contain a precipitate. This is achieved by adding acetic acid to reaction mixtures to prevent the precipitation of the zinc acetate-peroxide complexes. In contrast to the teachings of Danna '322, the present invention uses a zinc and HP mixture in an aqueous carrier which contains precipitate, or a suspension of particles, or colloid.

Zinc acetate dissolved in water gives a solution with a pH of 5 to 6 (Merck Index, 10th edition © 1983, page 1455, entry #9926). Thus, even before the addition of acetic acid, the formulations disclosed by Danna '322 have an acidic pH. Addition of acetic acid to the formulations lowers the pH even further.

Zinc peroxide can be synthesized using zinc acetate as a starting material (see "*Synthesis of Stabilized Nanoparticles of Zinc Peroxide*", Rosenthal-Toib, et al, *Chemical Engineering Journal* 136 (2008) p 425-429); wherein, solutions of zinc acetate and HP are treated with NaOH to raise the pH, and a precipitate is formed, collected, washed, and dried to give solid zinc peroxide (ZP). The product may be heat-treated at 300° C. to give zinc oxide (ZO). If a stabilizer, such as PEG200 is added to the ZA/HPP solutions, the final ZP or ZO particles are smaller in size (nanoparticles). Similarly to the work of Danna '322, only stoichiometric zinc acetate (2:1 Ac:Zn) is utilized as a precursor. Presumably, the drying step would evolve appreciable quantities of acetic acid, since the precursor solution has essentially the same composition as that disclosed by Danna '322.

The zinc acetate formulations of Danna '322 reportedly constitute some improvements over earlier patents by Welch et al. (U.S. Pat. Nos. 4,115,422 and 4,174,418) that disclose a similar system wherein zirconium acetate is used rather than zinc acetate. In a later patent by Vigo et al. (U.S. Pat. No. 5,656,037), magnesium acetate is utilized in place of zinc acetate or zirconium acetate, allowing reportedly greater temperature stability of the antimicrobial reaction products. Both of these variations nevertheless utilize significant concentrations of acetate in the treatment formulations, and in the finished textiles, and manifest the same disadvantages described above.

A nonwoven wipe impregnated with an aqueous solution of zinc acetate peroxide is disclosed by Corey in U.S. Pat. No. 5,152,966.

SUMMARY

This invention relates to processes for preparing an antimicrobial treatment formulation and binder compositions. The invention also relates to an antimicrobial treatment formulation comprising an acetate-free complex of a metal derivative and hydrogen peroxide which imparts durable antimicrobial activity to textiles treated with the treatment formulation. Typically, a 3-log to 6-log reduction of bacteria, even after 50 laundering cycles, is observed. Furthermore, the textiles treated with the antimicrobial treatment formulation are environmentally friendly, laundry-durable and antimicrobial. In addition, the antimicrobial treatment formulation can be used on white, colored, natural, and synthetic fibers as well as combinations thereof.

This invention also relates to methods of preparing the antimicrobial treatment formulation and methods for treating textiles with the antimicrobial treatment formulation to impart durable antimicrobial activity to textiles. The antimicrobial treatment formulation is prepared from a metal derivative, hydrogen peroxide and a source of hydroxide ion. The acetate-free treatment formulation may be an aqueous solution or a dispersion, suspension, coacervate, or emulsion in an aqueous carrier. The antimicrobial treatment formulation is acetate-free, wherein the amount of acetic acid (CH3COOH) or acetate (CH3COO—) groups in the formulation is low enough to avoid the generation of undesirable effects including odors, fumes, degradation of materials or equipment, staining, toxicity, irritation, environmental hazards, or safety hazards due to the presence of acetic acid or acetate.

The metal derivative may be in the form of a salt, ion, or complex. Preferred is a metal salt, ion, or complex of magnesium, zinc, aluminum, or zirconium. Most preferred is a salt, ion, or complex of zinc. The metal derivative will generally be a soluble salt of a metal ion wherein the negatively-charged counterion does not produce undesirable effects, such as evolution of acetate or acetic acid. Metal salts with inorganic counterions such as chloride, bromide, nitrate, or sulfate are preferred. Also preferred are one or more chloride, bromide, nitrate, or sulfate salts of magnesium, zinc, or zirconium. It is an aspect of this invention that the metal derivative is a mixture of a chloride salt and a nitrate salt. In a preferred embodiment of this invention, the metal derivative is comprised of a mixture of zinc chloride and zinc nitrate.

Hydrogen peroxide used in preparing the antimicrobial treatment formulation is typically an aqueous solution of hydrogen peroxide. The weight percentage of hydrogen peroxide in the treatment formulation may range from 0.2% to 50%, and the range of from 0.5% to 10% is preferred. Most preferred is a hydrogen peroxide weight percentage of about 2% to 6%.

A variety of sources of hydroxide ion may be used. Preferred sources of hydroxide ion include sodium hydroxide and potassium hydroxide. Hydroxide ion is used to neutralize the acidity of the metal derivative. The addition of a significant amount of hydroxide may be required in order to effect a noticeable rise in pH of the mixture, because the mixture generally has a high acidic buffer capacity (as described below). Addition of hydroxide also reduces the solubility of the metal ion via formation of species such metal hydroxides. This reduced solubility results in better durability (washfastness, or laundering stability) of the final antimicrobial materials after treatment. Textiles treated with the compositions have significant durable antimicrobial activity.

The antimicrobial treatment formulation or the complex of a metal derivative and hydrogen peroxide may be applied to a substrate, for example a textile, using methods known in the art, including, but not limited to, spraying, dipping, infusing, brushing, padding, or rolling. A textile treated with an antimicrobial treatment formulation of this invention does not exhibit any significant objectionable odor (such as a "vinegar" smell) after it has been thoroughly dried, nor does it contain residual volatile acids. When the antimicrobial treatment formulations and methods of this invention are properly employed, the treated textile shows no significant or objectionable discoloration, staining, or other adverse aesthetic effects as a result of the antimicrobial treatment, even if the textile is a colored or dyed textile. Textiles treated according to the methods described herein show significant durable antimicrobial activity and have up to a 6-log reduction of bacteria including *Staphylococcus aureus, Escherichia coli*, and *Klebsiella pneumoniae* when tested according to methods described herein.

The antimicrobial treatment formulation is a colloidal suspension of metal hydroxides, oxides, complexes, and/or peroxides. The suspension generally has a milky-white appearance, and solid white particulates may be visually observed in the suspension. Direct use of the as-prepared colloidal suspension may leave undesirable white residues or deposits on the surface of fabrics treated with said suspension. This is most noticeable on dark colored fabrics. These deposits can be eliminated by homogenization to reduce particle size prior to application to the fabric. It has been found that a suspension which readily passes through a mesh filter having a nominal pore opening of approximately 200 microns does not produce any visible residue on common dark-colored woven or knitted fabrics composed of cotton, polyester, or a blend thereof. It is therefore an aspect of this invention to homogenize the antimicrobial treatment formulation, and to pass it though a filter with a 200 micron pore size prior to use. Homogenization may be achieved using common homogenization equipment such as blenders, high-shear mixers, colloid mills, or ultrasonic devices.

It is an aspect of this invention that the antimicrobial treatment formulation of this invention may further comprise EDTA, or a salt of EDTA which is used to sequester iron. The presence of dissolved iron can decompose hydrogen peroxide and, therefore, interfere with the formation of the complex of hydrogen peroxide, metal derivative, and hydroxide ion. A preferred salt of EDTA is EDTA tetrasodium salt. One skilled in the art will recognize that other chelating agents may also be used to sequester iron.

It is an aspect of this invention that the antimicrobial treatment formulation may further comprise a durability-enhancing agent which is miscible, soluble, or dispersible in aqueous media and may be a component of the acetate-free complex of this invention comprising a metal derivative and hydrogen peroxide. Generally, less than approximately 1% by weight of the durability-enhancing agent is incorporated into the antimicrobial treatment formulation. Said durability-enhancing agent may be added to said treatment formulation as a suspension, emulsion, dispersion, or solution. Said durability-enhancing agent may be a polymer, a long-chain fatty acid, or a salt of a long-chain fatty acid, a polymeric amine, a fabric softener, or a lubricant. Sodium stearate is a preferred long-chain fatty acid durability-enhancing agent. Poly(ethyleneimine), also known as PEI, is a preferred polymeric amine durability-enhancing agent. Preferred fabric softener or lubricant durability-enhancing agents are those comprising emulsified polyolefins (such as polyethylene). Preferred softeners or lubricants include Acralube CP and Acralube CG (manufactured by Peach State Laboratories (Dalton, Ga.), and other compositions with similar chemical and physical properties. Combinations of two or more durability-enhancing agents may be used in the practice of this invention.

It is an aspect of this invention that additives, such as UV inhibitors, processing aids, softeners, antistatic agents, colorants, dyes, indicators, drugs, oils, lubricants, microspheres, temporary visual indicators, nutrients, growth factors, vitamins, emollients, moisturizers, scents, perfumes, and the like may be incorporated into the antimicrobial treatment formulation.

The formulations and methods of the present invention are suitable for application to various textile materials, including both natural and synthetic materials, as well as blends. The formulations and methods of the present invention are also suitable for application to various substrates, including woven, knitted, and non-woven textiles, polymers, films, fibers, or tapes. The substrates treated by the materials and methods of his invention may comprise all or part of a wound dressing, a burn dressing, a sanitary pad, incontinence pad a tampon, an intrinsically antimicrobial absorbent dressing, a diaper, toilet paper, a sanitary wipe, a sponge, a cotton swab, a surgical gown, an isolation gown, a lab coat, a glove, surgical scrubs, a head cover, a hair cover, a face mask, a suture, a floor mat, a lamp handle cover, an exam table cover, a cast liner, a splint liner, padding, gauze, packaging materials, a mattress cover, bedding, a sheet, a towel, clothing, underwear, a sock, shoe-cover, an automobile air filter, an airplane air filter, an HVAC system air filter, a protective garment for military or other use, an apparatus for protection against a biohazard or biological warfare agent, food packaging material, meat packaging material, fish packaging material, apparel for food handling, a surface for food preparation, carpet, wood, lumber, paper, and paper currency.

Textiles treated with the antimicrobial treatment formulations of this invention are found to be resistant to discoloration as exemplified by the testing results in the Examples, as described herein.

The antimicrobial treatment formulations and methods of the present invention may be used for the manufacture of an adhesive, a pressure-sensitive adhesive, a paint, a latex paint, an acrylic latex paint, a lacquer, a varnish, a sealant, a coating, a shellac, a caulk, or a water-repellant coating having antimicrobial properties. The acetate-free treatment formulations of the present invention may used in the manufacture of pressure-treated lumber, gypsum wallboard, or other building materials to increase resistance to attack and degradation of the materials by microorganisms. The acetate-free antimicrobial treatment formulations of this invention may also be used in the manufacture of antimicrobial wound dressings.

The antimicrobial treatment formulations of this invention may be used to neutralize, deactivate, or destroy certain chemical substances, for example chemical warfare agents when applied to a protective device. The antimicrobial treatment formulation may be applied to a protective device such as a garment, glove, mask, shelter, tent, screen, or curtain to offer protection against exposure to toxic or hazardous chemical agents.

It is an aspect of this invention to provide an acetate-free and substantially peroxide-free aqueous binder composition, comprising a metal derivative, and a source of hydroxide ion that may be combined at a later time with hydrogen peroxide and subsequently used for treating a substrate and imparting durable antimicrobial activity to said substrate. Said binder composition is similar in composition to the other antimicrobial treatment formulations described herein; however, the hydrogen peroxide component of the binder composition is withheld or substantially reduced. Such a composition has benefit in that stability may be increased, and safety and storage or shipping concerns will be minimized due to absence of oxidizing agent (hydrogen peroxide).

Definitions

"Microbe" or "microorganism" refers to any organism or combination of organisms such as bacteria, viruses, protozoa, yeasts, fungi, molds, or spores formed by any of these.

"Antimicrobial" refers to the microbicidal or microbistatic properties of a compound, composition, formulation, article, or material that enables it to kill, destroy, inactivate, or neutralize a microorganism; or to prevent or reduce the growth, ability to survive, or propagation of a microorganism.

"Substrate" refers to a surface or medium, such as a textile material, upon which an antimicrobial, such as the acetate-free antimicrobial treatment formulation of the invention, is applied, infused, or bonded.

"Surface" refers to the common outside surface of the substrate, and also to the internal surfaces of fibers, voids, channels, or pores within the substrate.

"Article" refers to a wide variety of products that can incorporate antimicrobial substrates. Examples of articles include, but are not limited to, household products, soaps, textiles, fabrics for hospital use, adhesive materials, wound dressings, sanitary pads, sponges, masks, mats, liners, tables, packaging materials, filters, garments, carpeting, wood, and currency.

"Durable" means that the antimicrobial activity of a material or a treated substrate remains after the material or treated substrate is washed or laundered one or more times, or that the antimicrobial activity persists for a significant portion of the expected useful lifetime of the treated substrate under normal use conditions.

"Metal Derivative" means an ion, salt, complex, hydrated ion, an ionic complex, a complex of an ion with hydrogen peroxide, a metal hydroxide species, a metal oxide species, or a metal peroxide species, or mixtures thereof, derived from one or more metallic elements for use in the invention. Preferred for use in this invention are metal derivatives of zinc, magnesium, or zirconium. For the purposes of this invention, the alkali metals (lithium, sodium, potassium, rubidium, cesium, and francium) are not included in the definition of "metal"; however, those elements also may be present in the formulations described herein.

"Acetate-free" means the molar concentration of acetic acid or acetate groups in the "acetate-free complex", the "acetate-free treatment formulation", or acetate-free binder composition is generally less than approximately 10% of the molar concentration of the metal derivative, and no acids or salts comprising acetate or other volatile carboxylic compounds are added to, or present in, the formulation or complex prior to use, at a level greater than approximately 10% of the molar concentration of the metal derivative. Acetate-free also means that the acetate content is below the threshold where no odor of acetate or acetic acid is detectable during treatment or drying.

"Durability-enhancing" and "durability-enhancement" mean that an article treated with the antimicrobial treatment formulation maintains a higher level of antimicrobial efficacy after repeated use or laundering than an article treated with a similar formulation that does not contain durability-enhancing agent.

BRIEF DESCRIPTION OF THE DRAWING

FIG. 1 illustrates the neutralization titration plot of 100 grams of solution containing zinc chloride (1 gram) and hydrogen peroxide (5.7 grams of 35%) with 4M sodium hydroxide. The drawing shows that the pH of the solutions rises abruptly after the addition of 4 mL of sodium hydroxide solution. Initially, the addition of a significant amount of hydroxide initially has little effect on the pH of the composition; however, this addition of hydroxide does contribute to the efficacy of the treatment formulation by reducing the solubility of the metal complex. This plot shows that the degree of neutralization of the treatment formulation cannot be accurately characterized solely by measurement of pH, as there is a significant region where pH does not vary strongly with neutralization.

DETAILED DESCRIPTION

We have demonstrated that textiles treated with a formulation made by the method disclosed in Danna '322, using zinc acetate, gave highly durable antimicrobial efficacy after 50 launderings. However, we have discovered that acetate is not a necessary component of an antimicrobial textile treatment based on metallic complexes of hydrogen peroxide (HP). One of ordinary skill in the art might surmise that the problem of acetic acid fume evolution and retention of residual acetate in the finished textiles could be alleviated entirely by simply modifying the method of Danna '322 to use zinc chloride (for example) in place of zinc acetate. In fact, we have found that the textile treated with a zinc chloride/hydrogen peroxide formulation lacked any antimicrobial efficacy after only two laundering cycles. In a similar experiment, a textile treated with a solution consisting of 5% magnesium chloride hexahydrate and 8.8% HP (sample #012009A) showed antimicrobial efficacy; however is was substantially lost after only two laundering cycles. These were unexpected results, which would seem to indicate that acetate ion is definitely required for the formation of laundry-stable antimicrobial textiles via treatment with solutions of zinc or magnesium ion and hydrogen peroxide. Yet, in accordance with this invention, we have subsequently found otherwise Aqueous zinc chloride is quite acidic, having a pH of approximately 4 (Merck Index, $10^{th}$ edition—c 1983, page 1456, entry #9932). Our experiments revealed that an aqueous solution of 1% zinc chloride and 2% hydrogen peroxide generally has a measured pH of about 4.5. A concentrated solution of zinc nitrate (17% zinc content) obtained from a commercial source (Golden Eagle) exhibits a pH of approximately 1.0.

We have performed experiments to test how a ratio of acetate to zinc lower than that suggested by Danna affected the antimicrobial properties of the treated textiles. Danna discloses a "baseline" Ac:Zn ratio of 2 to 1 in the treatment solution when no acetic acid is added to further solubilize the complex, and prevent formation of precipitates. We found that when mixtures of sodium acetate and zinc chloride were used (with 2% HP), antimicrobial efficacy after laundering was essentially zero when no acetate was present. We found that significant post-laundering antimicrobial efficacy was present when the molar acetate concentration was greater than, or equal to, approximately ¼ that of chloride (i.e. two moles of chloride, and 0.5 moles of acetate). Only slight post-laundering antimicrobial efficacy was observed when the molar acetate concentration was 1/10 that of chloride. These experiments were all performed at native pH (no adjustment), which is generally less than 5, and the treatment solutions were clear and homogenous.

We have found that a considerable portion of the solid product formed upon drying an acidic aqueous solution containing zinc, acetate, and HP (as taught by Danna) is actually soluble in water (easily re-dissolves); however, it is reasonable to expect that it is only the insoluble components of this reaction product that can be retained on a textile substrate to impart durable (laundering-proof) antimicrobial activity.

Note that the results, observations, and conclusions described above pertain to aqueous mixtures of zinc chloride, acetate salts, and hydrogen peroxide with an as-produced, acidic, pH. No intentional neutralization or pH adjustment was done, i.e. no hydroxide or basic reagent was added, and all the solutions generally had a pH between 4 and 5.5. In other words, when mixtures of zinc acetate and hydrogen peroxide are used to treat textiles, durable antimicrobial efficacy is observed, even without neutralization or pH adjustment; however, simply substituting zinc chloride for zinc acetate, while eliminating the potential for generation of undesirable acetic acid fumes, does not result in durable antimicrobial efficacy.

As described above, the volatility of acetic acid as a reagent and a reaction by-product causes problems. We have tried to replace the use of acetate in the prior art formulations and methods of Danna with less volatile carboxylic species such as citrate, tartrate, gluconate, benzoate, or succinate. However, we found that substrates treated with such carboxylic species in place of acetate did not manifest durable antimicrobial activity. On the other hand, several volatile carboxylic species such as formate, and propionate did give materials with durable antimicrobial activity; however, the generation of acidic fumes was still a considerable problem with this approach.

We have determined that if the acidity of such solutions is wholly or partially neutralized by addition of a hydroxide source, that the species therein become substantially less soluble. The addition of a hydroxide source generally leads to formation of a precipitate; however, the pH may not change significantly, even when significant hydroxide is added (see FIG. 1). The formation of insoluble species allows the treated substrate to retain a greater amount of active antimicrobial, and less of the deposited antimicrobial is subsequently dissolved during laundering, which means the antimicrobial effect is more durable. The efficiency of the process is thus increased, as it is possible to obtain the same level of durable antimicrobial activity while using a lower concentration of reagents.

Furthermore, we found that if the acidity of the treatment solutions is wholly or partially neutralized by addition of a hydroxide source, it is possible to produce treated textiles having significant durable antimicrobial activity, even when acetate is completely eliminated from the solution. For example, an aqueous solution composed of 1 weight percent zinc chloride and 2% hydrogen peroxide, was adjusted to pH=7.5 using 4M NaOH. The addition of NaOH (a source of hydroxide ion) caused the formation of a considerable amount of finely-dispersed white precipitate. This precipitate did not agglomerate or settle readily, and was easily re-dispersed by mild agitation, stirring, or mixing. A green-dyed textile material was thoroughly wetted with this suspension, then passed through a roller press to expel excess liquid, leaving a damp textile with approximately 100% weight gain. The damp textile was then dried. Of course, no acetic acid odor or fumes were given off during this process, since no acetate was contained in the treatment solution. The treated textile did not exhibit any objectionable odor, nor did it contain any acidic residues. The textile showed no staining, discoloration, or other adverse aesthetic effects. It was found that the treated textile showed significant durable antimicrobial activity (~6-log reduction of bacteria), even after 50 laundering cycles, when tested by methods described herein. This constitutes a significant useful improvement over the method of Danna. Addition of hydroxide also converts soluble metal species (such as zinc chloride or zinc nitrate), to insoluble species (such as zinc hydroxide and insoluble zinc-peroxide complexes), which results in improved durability of the antimicrobial products, since insoluble species are harder to wash off.

In the experiments and examples described herein, the pH of initially acidic solutions containing zinc ion was raised by the addition of NaOH to a specified level (i.e. pH=7.5). Although it was found that the durable antimicrobial efficacy of a treated textile is significantly improved by increasing the pH of the zinc and hydrogen peroxide treatment solution, it is not specifically the pH which causes this effect. While we do not wish to be bound by any particular theory, we believe that it is the reaction of hydrated zinc ion with hydroxide ion to form zinc hydroxides or hydroxide-like complexes which causes the enhanced antimicrobial effect. The observed pH change is merely an artifact which enables one to discern when a sufficient amount of hydroxide has been added. The conversion of hydrated zinc chloride to hydrated zinc hydroxychlorides (and the related complexes with HP) results in the formation of visible precipitates, as described above. Presumably, these precipitates react, upon drying, to form antimicrobially-active residues with lower solubility than the corresponding residues which are formed when the treatment solutions are not modified by addition of a hydroxide source.

If an aqueous mixture of zinc chloride and HP is titrated with NaOH, a plot pH versus amount of NaOH added shows a sigmoid shaped curve (see FIG. 1), with an initial flat area wherein the pH does not change much with addition of base (hydroxide). At approximately pH=6.0, there starts a sharp pH jump, centered at around pH=7.5, which levels-off above pH=9. The initial low pH plateau apparently represents an area where added hydroxide is reacting with hydrated zinc ions, zinc chloride complexes, and/or zinc hydroxide species—or their hydroperoxide equivalents—to produce complexes with more zinc hydroxide-like character. Although the pH of the solution is not initially affected by the addition of a hydroxide source, the acidity is still being neutralized. The acidic buffer capacity of the mixture is being reduced as hydrated zinc ions are converted to hydroxide species. The sharp pH jump shown in FIG. 1 most likely indicates where this conversion has been essentially completed. Zinc hydroxide species are inherently less soluble than simple hydrated zinc ions, and since the durability of a treated substrate will be better when the deposited material is less soluble, it is believed that retention of the antimicrobial metal-hydrogen peroxide complexes, and hence durable antimicrobial efficacy will become better as this neutralization reaction proceeds.

Since the pH does not change significantly during the early course of this reaction, pH is not a useful tool to monitor the progress at the initial stages of neutralization; however, the observation of a sudden jump to pH above 7.0 serves as a very useful indicator that the solution has obtained the correct properties in order to be useful to produce durable antimicrobial efficacy when used to treat a textile substrate. The midpoint of the titration shown in FIG. 1 (pH=7.5) represents roughly an addition of 0.0140 moles of hydroxide ion to the 0.0074 moles of zinc ion present. This is essentially a 2:1 ratio of hydroxide to zinc. Note that the exact ratio may differ depending on the presence of other acidic species in the mixture. Although the durable antimicrobial efficacy resulting from a treatment solution with a pH of 7.5 or higher may be greater than for a less-neutralized solution, it is found in practice that higher neutralization also produces a more copious precipitate which may be more difficult to apply to the substrate in a uniform manner. Furthermore, it is found that at basic pH the reactivity (i.e. instability) of hydrogen peroxide is increased. This shortens the useful storage life of the composition, and can result in undesirable effects such as bleaching of colored substrates. Furthermore, increasing neutralization adds solids content to the treatment formulation and may decrease the solubility of the dried material since the neutralization by-product (NaCl) is highly water soluble. Therefore, the optimum degree of neutralization for practice of this invention is generally somewhere between 50% and 100% (where 100% equals the amount of hydroxide required to raise the pH to approximately 7.5).

It is an aspect of this invention that an acetate-free treatment formulation comprising metal derivative and hydrogen peroxide is used to impart durable antimicrobial efficacy to a substrate. Said treatment formulation may comprise a solution, suspension, dispersion, or colloid. A preferred metal derivative is a zinc derivative. The zinc derivative may be in the form of hydrated zinc ion, an ionic complex of zinc ion, a complex of zinc ion with hydrogen peroxide, or a zinc hydroxide species, or combinations thereof.

The source of the metal derivative used in the antimicrobial treatment formulation will generally be a soluble metal salt, wherein the negatively-charged counterion portion of the salt does not produce undesirable effects, such as evolution of acid fumes. Metal salts with inorganic counterions such as chloride, bromide, nitrate, or sulfate are preferred. It is an aspect of this invention that the metal derivative for the antimicrobial treatment formulation is a mixture of a chloride salt and a nitrate salt, whereby the mixture reduces the potential corrosive effects of a chloride-containing solution. In a preferred embodiment of this invention, the source of the metal ion for the antimicrobial treatment formulation is a mixture of zinc chloride and zinc nitrate. The preferred molar ratio of zinc chloride to zinc nitrate is between 1:2 and 2:1. A more preferred molar ratio of zinc chloride to zinc nitrate is 1:1. Lowering the amount of zinc chloride in the mixture to give a molar ratio of zinc chloride to zinc nitrate less than approximately 1:2 may result in the formation of thick gelatinous precipitates which are difficult to use for treating textiles.

The treatment formulation may also comprise a source of hydroxide ion. In general, it is desirable that at least 25% of the amount of hydroxide ion which would be required to raise the pH of the acetate-free mixture comprising metal derivative and hydrogen peroxide from its initial pH value to a pH of 7.5 be added in order to obtain a treatment formulation capable of imparting durable antimicrobial activity to a substrate. It is more desirable that between 50% and 100% of the amount of hydroxide ion which would be required to raise the pH of the acetate-free mixture comprising metal derivative and hydrogen peroxide from its initial pH value to a pH of 7.5 be added in order to obtain a treatment formulation capable of imparting durable antimicrobial activity to a substrate. It is even more desirable that 75% of the amount of hydroxide ion which would be required to raise the pH of the acetate-free mixture comprising metal derivative and hydrogen peroxide from its initial pH value to a pH of 7.5 be added in order to obtain a treatment formulation capable of imparting durable antimicrobial activity to a substrate.

In a preferred embodiment of this invention, the concentration of metal in the acetate-free treatment formulations is at least 0.05% by weight. In a more preferred embodiment, the concentration of metal derivative in the substantially acetate-free treatment formulation is at least 0.250% by weight. In a still more preferred embodiment, the concentration of metal derivative is at least 0.75% by weight. In an even more preferred embodiment, the concentration of metal derivative in the substantially acetate-free treatment formulation is at least 1.5% by weight. In a most preferred embodiment, the concentration of metal derivative in the acetate-free treatment formulation is at least 3.00% by weight. The cited concentrations refer to the elemental metal component only, not including the weight of any associated counterions, ligands, or complexed species. The preferred ranges specified in this paragraph refer to optimization of antimicrobial efficacy only. One skilled in the art will realize that higher concentrations will add cost, or that other factors may dictate the use of lower levels.

In a preferred embodiment of this invention, the molar ratio of hydrogen peroxide to zinc in the acetate-free treatment formulation is 1:1. In a more preferred embodiment of this invention, the molar ratio of hydrogen peroxide to zinc in the acetate-free treatment formulation is 2:1. In an even more preferred embodiment of this invention, the molar ratio of hydrogen peroxide to zinc in the acetate-free compositions is 3:1. In a most preferred embodiment of this invention, the molar ratio of hydrogen peroxide to zinc in the acetate-free treatment formulation is 4:1. The preferred ranges specified in this paragraph refer to optimization of antimicrobial efficacy only. One skilled in the art will realize that higher ratios will add cost, or that other factors may dictate the use of lower levels.

It is an aspect of this invention that a acetate-free treatment formulation prepared by combining metal derivative, water, hydrogen peroxide, and (optionally) a source of hydroxide ion is used to impart durable antimicrobial efficacy to a substrate. Said treatment formulation may comprise a solution, suspension, dispersion, or colloid. In a preferred embodiment of this invention, the source of hydroxide ion is capable of providing 0.50 moles of hydroxide for every mole of zinc in the treatment formulation. In a more preferred embodiment of this invention, the source of hydroxide ion is capable of providing between 1.0 and 2.0 moles of hydroxide for every mole of zinc in the treatment formulation. In a most preferred embodiment of this invention, the source of hydroxide ion is capable of providing at least 1.5 moles of hydroxide for every mole of zinc in the treatment formulation.

The sources of hydroxide ion in the practice of this invention will be agents that are familiar to one skilled in the art. Preferred sources of hydroxide ion in the practice of this invention include sodium hydroxide and potassium hydroxide.

It is an aspect of this invention that the acetate-free treatment formulation comprising metal derivative and hydrogen peroxide also comprises a durability-enhancing agent which is miscible, soluble, or dispersible in aqueous media. Said durability-enhancing agent may be a polymer such as polyvinyl alcohol, or copolymers thereof, and may be added to said treatment formulation as a suspension, emulsion, dispersion, or solution. Said durability-enhancing agent may also be a long-chain fatty acid, or a salt thereof. Preferred durability-enhancing agent are sodium or potassium salts of C12-C20 fatty acids. A preferred durability-enhancing agent is sodium stearate. When sodium stearate is used as a durability-enhancing agent, the concentration is preferably at least 0.1 weight % in the treatment formulation, in a more preferred embodiment, the concentration of sodium stearate durability-enhancing agent is at least 0.25%, and in a most preferred embodiment, the concentration of sodium stearate durability-enhancing agent is at least 0.50%. In a preferred embodiment, the sodium stearate is added to the treatment solution in the form of an aqueous solution containing between 1 and 10% sodium stearate, said solution having a melting point of approximately 60° C. It is preferred to add the sodium stearate solution as a liquid in order to achieve uniform mixing prior to further homogenization.

Said durability-enhancing agent may be a polymeric amine. A preferred durability-enhancing agent is poly(ethyleneimine), also known as PEI. Generally, less than 1% by weight of PEI is incorporated into the antimicrobial treatment formulation in order to effect said durability-enhancement. When PEI is used as a durability-enhancing agent, the concentration is preferably at least 0.1 weight % in the treatment formulation, in a more preferred embodiment, the concentration of PEI durability-enhancing agent is at least 0.25%, and in a most preferred embodiment, the concentration of PEI durability-enhancing agent is at least 0.50%. In a preferred embodiment, the PEI is added to the treatment solution in the form of an aqueous solution containing between 1 and 10% PEI.

The durability-enhancing agent may also be a fabric softener or textile lubricant. Preferred softeners and lubricants are those comprising emulsified polyolefins such as polyethylene. Preferred softeners or lubricants include Acralube CP and Acralube CG (manufactured by Peach State Laboratories (Dalton, Ga.), and other formulations with similar chemical and physical properties. In a preferred embodiment of this invention the concentration of softener or lubricant is at least 0.5%, in a more preferred embodiment, the concentration of softener or lubricant is at least 1%, and in a most preferred embodiment, the concentration of softener or lubricant is at least 2%.

Combinations of two or more durability-enhancing agents may be used in the practice of this invention. Durability-enhancing agents will generally be added to the formulation prior to homogenization.

It is well known that hydrogen peroxide reacts spontaneously with dissolved iron (Fenton's Reaction). This reaction decomposes hydrogen peroxide, and thus the presence of dissolved iron will interfere with the formation of the antimicrobial compositions. The activity of iron can be sequestered with a chelating agent, for example, EDTA (ethylenediaminetetraacetic acid). It is therefore an aspect of this invention that EDTA, or a sodium salt of EDTA is added to the treatment solution in order to stabilize hydrogen peroxide against decomposition by iron. The treatment solution may be exposed to iron during contact with processing equipment, or iron may even be present in the process water used to prepare the treatment solution. Addition of a chelating agent such as EDTA stabilizes the treatment solution during use and storage. One skilled in the art will recognize that other chelating agents may also be used to sequester iron. In a preferred embodiment of this invention, the treatment solution comprises at least 0.01 weight % EDTA. In a most preferred embodiment, the treatment solution contains at least 0.05% EDTA.

It is unexpected that an aqueous suspension containing a significant content of insoluble solid or visible precipitate can be uniformly applied to a textile substrate without causing some degree of staining, discoloration, or other adverse aesthetic effects. The prior art of Danna teaches that treatment solutions must be kept acidic in order to prevent formation of insoluble precipitates. Unfortunately, Danna's approach, as explained above, leads to numerous problems, such as acid fume generation, wasteful consumption of chemicals, and lower efficacy (durable antimicrobial activity) at a given treatment level (metal content). All of these problems present cost issues which could make the technology commercially unattractive. In the current invention these issues have been overcome by eliminating the use of acetate.

The treatment formulations used to prepare the antimicrobial treated articles of this invention are colloidal suspensions or dispersions of metal hydroxides, oxides, and/or peroxides. These suspensions generally have a milky-white appearance, and solid white particulates may be visually observed in the suspensions. Direct use of the as-prepared colloidal suspensions may leave undesirable white residues or deposits on the surface of fabrics treated with said suspension. This is most noticeable on dark colored fabrics. These deposits can be eliminated by homogenization to reduce particle size prior to application to the fabric. It has been found that suspensions which readily pass through a mesh filter having a nominal pore opening of approximately 200 microns do not produce any visible residue on common dark-colored woven or knitted fabrics composed of cotton, polyester, or blend thereof. It is therefore an aspect of this invention to homogenize the treatment formulation, and to pass them though a filter with a 200 micron or smaller pore size prior to use. Homogenization may be achieved using common homogenization equipment such as blenders, high-shear mixers, colloid mills, or ultrasonic devices.

The advantages of the current improved method and formulations for preparing antimicrobial textiles with good laundering durability have been demonstrated in laboratory experiments, and also in pilot-scale production runs conducted at a commercial textile manufacturing plant. Details of the laboratory experiments and pilot-scale production runs are given in the examples below. The results of the pilot-scale production run confirmed the laboratory findings that neutralization of the treatment solutions by addition of hydroxide, and elimination of acetate and acetic acid from the treatment formulations resulted in improved laundering durability of antimicrobial textile treatments, even at low concentrations of treatment solution. Improvements in the physical and aesthetic properties of the treated textiles as a result of these changes were also confirmed. A financial cost benefit is also realized due to the improved method and formulations—due, in part, to the overall lower amount of chemicals needed, the fact that zinc chloride is cheaper than zinc acetate, and elimination of the need for costly rinsing and additional drying steps. Furthermore, the improved process offers significant benefits with regard to regulatory, environmental, health and safety issues.

It is an aspect of this invention that an antimicrobial textile is produced by treating a substrate with the treatment formulation of this invention.

It is an aspect of this invention that an antimicrobial textile prepared using the materials and methods of this invention is capable of effecting a reduction of viable bacteria when approximately 0.5 mL of aqueous liquid which contains approximately 1,000,000 viable bacterial organisms contacts three square inches of the antimicrobial textile. In a preferred embodiment of this invention, the materials and methods of this invention produce a reduction of viable bacteria so that less than 1,000 viable organisms remain (3-log reduction). In a more preferred embodiment of this invention, said reduction of viable bacteria is such that less than 100 viable organisms remain (4-log reduction). In an even more preferred embodiment of this invention, said reduction of viable bacteria is such less than 10 viable organisms remain (5-log reduction). In a most preferred embodiment of this invention, said reduction is such that zero viable organisms remain (6-log reduction, or full-kill). In a preferred embodiment of this invention, said reduction of viable bacteria occurs within 24 hours. In a more preferred embodiment of this invention, said reduction of viable bacteria occurs in less than 10 hours. In a still more preferred embodiment of this invention, said reduction of viable bacteria occurs in less than 4 hours. In a still more preferred embodiment of this invention, said reduction of viable bacteria occurs in less than 2 hours. In an even more preferred embodiment of this invention, said reduction of viable bacteria occurs in less than 1 hour. In the most preferred embodiment of this invention, said reduction of viable bacteria occurs in less than 30 minutes.

In an embodiment of this invention, said reduction of viable bacteria is observed on the as-produced treated substrate or antimicrobial textile of this invention prior to any rinsing, washing, or laundering.

In a preferred embodiment, said reduction of viable bacteria is observed after the treated substrate or antimicrobial textile has been rinsed. In a more preferred embodiment, said reduction of viable bacteria is observed after the treated substrate or antimicrobial textile has been laundered. In an even more preferred embodiment, said reduction of viable bacteria is observed after the treated substrate or antimicrobial textile has been laundered 5 times. In an even more preferred embodiment, said reduction of viable bacteria is observed after the treated substrate or antimicrobial textile has been laundered 10 times. In an even more preferred embodiment, said reduction of viable bacteria is observed after the treated substrate or antimicrobial textile has been laundered 25 times. In a most preferred embodiment, said reduction of viable bacteria is observed after the treated substrate or antimicrobial textile has been laundered 50 times or more. In a preferred embodiment of this invention said reduction of viable bacteria occurs when laundering is conducted using cold water (<80° F.). In a more preferred embodiment of this invention said reduction of viable bacteria occurs when laundering is conducted using warm water (80 to 119° F.). In a most preferred embodiment of this invention said reduction of viable bacteria occurs when laundering is conducted using hot water (>119° F.).

A drying step is utilized in the practice of this invention. The textile substrate is dried after it has been treated with the antimicrobial treatment formulation. It is an aspect of the inventive method to use any temperature and time combination that results in thorough drying of said substrate.

As used herein, dried means, for instance, that a substrate exposed to the treatment formulation is then dried to a constant weight. As used herein, dried to a constant weight means dried to the point at which continued application of the chosen drying procedure will no longer result in a considerable additional measurable loss of weight due to evaporation of water or other solvent.

Attainment of constant weight is a useful tool to measure extent of dryness; however, the attainment of constant weight is not the actual factor that imparts the antimicrobial to the substrate. The particular temperatures and drying times necessary to achieve thorough drying depend, among other things, on the particular substrate material, the initial amount of moisture in the substrate, the weight and size of the substrate, the amount of airflow provided to the substrate during drying, and the humidity of the air or other medium contacting the substrate. Any drying apparatus, drying method, and temperature and drying time combination that thoroughly dries the treated substrate is sufficient. For purposes of illustration, depending on the particular characteristics of a particular application, the drying step may be performed in an oven (e.g. 80° C. for 2 hours), in a high throughput furnace (e.g. 140° C. for 30 seconds), in a clothes dryer, in a desiccator, in a vacuum chamber, in a dehumidifier, in a dehydrator, or in a lyophilizer (freeze dryer). Infrared heat, radiant heat, microwave, and hot air are all suitable drying methods for the substrate which has been exposed to the treatment formulation. The upper limit of drying temperature for a particular application will generally be determined by the degradation temperature of the particular substrate or peroxide. Other drying methods such as supercritical fluid drying may also be successfully employed in the practice of this invention. Freeze drying may be used. It is generally preferable that the treated article is not exposed to heat in excess of what is required to effect complete drying in a reasonable time.

It is an aspect of this invention that the substantially acetate-free treatment formulation may be applied to the substrate using methods known in the art, including but not limited to, spraying, dipping, infusing, brushing, padding, or rolling.

Excess substantially acetate-free treatment formulation may be removed by suitable methods known in the art, such as rolling, nipping, padding, centrifuging, wringing, or blotting, and the like, in order to control the amount of composition in the final treated material. Any mechanical action or force may be applied; however, it is preferred that such action or force be uniform in order to provide an even distribution of remaining composition within the loaded substrate as the treatment formulation is forced out. It should be noted application of a mechanical force to remove excess treatment formulation prior to drying is distinct from the drying procedure in that the mechanical force removes both the antimicrobial and the carrier solution, while the drying procedure removes only the carrier solution, through evaporation, but leaves the antimicrobial in the treated substrate.

Laboratory experiments have confirmed that the formulations and methods of the present invention are suitable for application to various textile materials, including both natural and synthetic materials, as well as blends. Textile substrates containing cotton, polyester, acrylic, nylon, and lycra have all been demonstrated to exhibit durable antimicrobial activity after treatment by the materials and methods of the current invention. The formulations and methods of the present invention are suitable for application to various substrates, including woven, knitted, and non-woven textiles.

Antimicrobial textiles, prepared using the acetate-free treatment formulation of this invention comprising metal derivative and hydrogen peroxide, are found to be resistant to discoloration. It is known that the products of some antimicrobial textile treatments such as those utilizing silver, quaternary ammonium compounds (quats), or polyhexamethylene biguanide (PHMB) are prone to discolor more than untreated textiles during use or laundering (see U.S. Pat. No. 5,700,742, for example). In the case of quats or biguanides such as PHMB, the positive electrostatic charge of the active agent tends to bind detergent, which in turn binds dirt or grease. Similarly, electrostatic attraction of anionic species such as dyes to the positively charged sites causes discoloration. In the case of silver-based technologies, the active agent itself can cause discoloration, especially after aging, or exposure to light. The antimicrobial textiles prepared using the acetate-free treatment formulations of the current invention do not discolor by these mechanisms, as demonstrated by the results of testing using standard methods, as described herein.

The acetate-free treatment formulation of this invention comprising metal derivative and hydrogen peroxide may be combined with an aqueous-based polymer emulsion used as, or for manufacture of, a pressure-sensitive adhesive. Said combination may be applied to a substrate, according to the methods of this invention, in order to produce a material having both adhesive and antimicrobial properties. Said adhesive may be used as a component of a self-adhesive article, such as a tape, label, bandage, wound dressing, or other article intended to be quickly and easily bonded to a surface.

The acetate-free treatment formulation of this invention comprising metal derivative and hydrogen peroxide may be combined with an aqueous-based polymer emulsion or a solution used as, or for manufacture of, a paint, a latex paint, an acrylic latex paint, a lacquer, a varnish, a sealant, a coating, a shellac, a caulk, or a water-repellant coating.

The acetate-free treatment formulation of this invention comprising metal derivative and hydrogen peroxide may be used in the manufacture of pressure-treated lumber which is resistant to attack and degradation by microorganisms. A treatment solution, such as those described herein, can be infiltrated, infused, or penetrated into a wood, timber, or lumber material using methods that will be familiar to one skilled in the art. This would generally include using negative pressure or vacuum to assist in penetration of the antimicrobial composition into the wood.

The acetate-free treatment formulation of this invention comprising metal derivative and hydrogen peroxide may be used in the manufacture of an antimicrobial wound dressing by applying the compositions to a suitable substrate such as a woven or nonwoven textile, a gauze, a bandage, a sponge, or other absorbent material. Since a wound dressing material is generally discarded after use rather than being laundered, a lower amount of antimicrobial composition is likely needed than is described herein for application to textiles intended for use as clothing. The as-prepared wound dressing may be rinsed prior to use, to remove soluble or leachable components which could migrate from the dressing into the body and possibly have undesirable effects such as cytotoxicity or delayed wound healing.

It is an aspect of the current inventive method that the substrates treated by the materials and methods of this invention comprise all or part of a wound dressing, a burn dressing, a sanitary pad, an incontinence pad, a tampon, an intrinsically antimicrobial absorbent dressing, a diaper, toilet paper, a sanitary wipe, a sponge, a cotton swab, a surgical gown, an isolation gown, a lab coat, a glove, surgical scrubs, a head cover, a hair cover, a face mask, a suture, a floor mat, a lamp handle cover, an exam table cover, a cast liner, a splint liner, padding, gauze, packaging materials, a mattress cover, bedding, a sheet, a towel, clothing, underwear, a sock, shoe-cover, an automobile air filter, an airplane air filter, an HVAC system air filter, a protective garment for military or other use, and adhesive, a tape, a label, an apparatus for protection against a biohazard or biological warfare agent, food packaging material, meat packaging material, fish packaging material, apparel for food handling, a surface for food preparation, carpet, wood, lumber, gypsum wallboard, paint, varnish, caulk, pressure sensitive adhesive, protective or decorative coatings, paneling, masonry, grout, tile, water-proofing treatment, pressure-treated lumber, litter or bedding for cats or other animals, paper, or paper currency.

It is an aspect of this invention that additives such as UV inhibitors, processing aids, softeners, antistatic agents, colorants, dyes, indicators, drugs, oils, lubricants, microspheres, temporary visual indicators, nutrients, growth factors, vitamins, emollients, moisturizers, scents, perfumes and the like may be incorporated into the acetate-free treatment formulation.

It is an aspect of this invention to provide an acetate-free and substantially peroxide-free aqueous binder composition for hydrogen peroxide, comprising a metal derivative, and a source of hydroxide ion; wherein, said binder may be combined with hydrogen peroxide and subsequently used for treating a substrate and imparting durable antimicrobial activity to said substrate. Said binder composition is similar in composition to the other acetate-free treatment formulations described herein; however, the hydrogen peroxide component of the composition is withheld or substantially reduced. Such a composition has benefit in that stability may be increased, and safety and storage or shipping concerns will be minimized due to absence of oxidizing agent (hydrogen peroxide). Said binder composition may be produced in a concentrated form. Said binder composition may be homogenized as part of its manufacturing process. Said binder composition may be mixed or diluted with hydrogen peroxide, and used to treat a substrate and impart durable antimicrobial activity to a substrate according to the methods described herein. The same preferred embodiments described for other aspects of this invention will apply to said binder composition, including the use of zinc chloride, zinc nitrate, amount of hydroxide source, and addition of components such as EDTA, durability-enhancing agents, PEI, salts of fatty acids, softeners, lubricants, and other additives. In other words, the binder composition may comprise any of the compositions defined by the aspects of the current invention, with the exception that hydrogen peroxide is withheld, or its concentration substantially reduced compared to the acetate-free treatment formulation described herein. The binder may be prepared in a concentrated form, preferably comprising at least twice the concentration of metal derivative and other additives described in the preferred aspects of the antimicrobial treatment solutions described herein; more preferably comprising at least three times the concentration of metal derivative and other additives described in the preferred aspects of the antimicrobial treatment solutions described herein; and most preferably comprising at least four times the concentration of metal derivative and other additives described in the preferred aspects of the antimicrobial treatment solutions described herein. The best performance and durable antimicrobial efficacy will be obtained if the required amount of HP is added to, and thoroughly mixed with, the concentrated binder prior to dilution of the binder or binder-HP mixture to the desired use concentration. Thus, it is preferable to add HP as a concentrated form (preferably as a 35% solution of HP, and more preferably as a 50% or greater solution of HP). Preferably, the HP is allowed to react with the concentrated binder for at least 20 minutes prior to dilution or use. More preferably, the HP is allowed to react with the concentrated binder for at least 60 minutes prior to dilution or use. Preferably, the mixture of concentrated binder and HP is continuously and thoroughly stirred, mixed, or agitated while it is being allowed to react, and prior to dilution or use. Preferably, the mixture of concentrated binder and HP is also homogenized prior to dilution or use.

It is an aspect of this invention that said acetate-free and substantially peroxide-free aqueous binder composition may be applied to a substrate in the absence of any additional hydrogen peroxide addition, and that the treated substrate can then be treated with hydrogen peroxide, either before or after drying, in order to produce a treated substrate which has antimicrobial properties.

The antimicrobial articles of this invention, prepared by treating a substrate with the compositions of this invention may loose some of its antimicrobial efficacy over time, after prolonged normal use, as a result of excessive laundering, or by other factors. It is an aspect of this invention that at least part of any such lost antimicrobial efficacy can be restored by exposing the article to hydrogen peroxide which will react with, become bound to the article, or otherwise act to restore at least some of the article's initial antimicrobial efficacy. Therefore, it is an aspect of this invention to provide a method of preparing an antimicrobial article having regenerable antimicrobial efficacy.

It is an aspect of this invention that the antimicrobial compositions, formulations and compositions, as well as the treated substrates, materials, or articles of this invention may be used to neutralize, deactivate, or destroy certain chemical substances. The antimicrobial compositions, formulations and compositions, as well as the treated substrates, materials, or articles of this invention comprise peroxide, and it is well-known that peroxides can act as oxidizers or oxidizing agents which can destroy, neutralize, or deactivate many different chemical species, including converting toxic chemicals to less toxic or nontoxic forms. For instance, hydrogen peroxide is known to react rapidly with hydrogen sulfide (a toxic gas), converting it to nontoxic sulfur and sulfate (see for instance, U.S. Pat. No. 4,574,076). Similarly, peroxides can be used to deactivate chemical warfare agents (U.S. Pat. No. 7,442,677). Thus, it is an aspect of this invention that a textile or other substrate treated using the formulations and compositions of this invention comprises a protective device (for example: a garment, glove, mask, or curtain, screen, tent, or shelter)

designed to shield a person or object against exposure to toxic or hazardous chemical agents, including chemical warfare agents.

The problem of corrosion and other undesirable effects resulting from the release of hydrogen sulfide into buildings constructed using contaminated gypsum drywall (wallboard) imported from China has gained much media attention lately (Tim Padgett, "Is Drywall the Next Chinese Import Scandal?" Time, Mar. 23, 2009). The compositions and methods of the present invention can be used to neutralize the volatile sulfide compounds being emitted from contaminated drywall. For example, contaminated drywall can be treated with a acetate-free composition comprising hydrogen peroxide as described herein. Alternatively, an acetate-free treatment formulation of this invention comprising metal derivative and hydrogen peroxide may be combined with an aqueous-based polymer emulsion or a solution used as, or for manufacture of, a paint, a latex paint, an acrylic latex paint, a lacquer, a varnish, a sealant, a coating, a shellac, a caulk, or a water-repellant coating, and the combination applied to contaminated drywall in order to prevent or neutralize the emission of toxic or corrosive volatile chemicals. Alternatively, the acetate-free treatment formulation of this invention may be incorporated into gypsum wallboard during its manufacture.

In light of the general disclosure provided herein above, with respect to the manner of practicing this inventive method, those skilled in the art will appreciate that this disclosure enables the practice of the inventive method as defined in the aspects described herein. However, the included experimental details are provided to ensure a complete written description of this invention, including the best mode thereof. However, it will be appreciated that the scope of this invention should not be construed in terms of the specific examples provided. Rather, the scope of this invention is to be apprehended with reference to the aspect described herein, in light of the complete description of this inventive method constituted by this entire disclosure.

It is to be understood that the present invention may have various other embodiments. Furthermore, while the form of the invention herein shown and described constitutes a preferred embodiment of the invention, it is not intended to illustrate all possible forms thereof. It will also be understood that the words used are words of description rather than limitation, and that various changes may be made without departing from the spirit and scope of the invention disclosed. The scope of the invention should not be limited solely to the examples given.

Concentrations, dimensions, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a weight ratio range of about 1 wt % to about 20 wt % should be interpreted to include not only the explicitly recited limits of 1 wt % and about 20 wt %, but also to include individual weights such as 2 wt %, 11 wt %, 14 wt %, and sub-ranges such as 10 wt % to 20 wt %, 5 wt % to 15 wt %, etc.

EXAMPLES

Example 1

Pilot-Scale Antimicrobial Textile Production Using a Solution Of Zinc, Acetate, Chloride, Acetic Acid, and Hydrogen Peroxide, at Low pH.

Comparative Example

This is a comparative example, which essentially follows the method of Danna et al. (U.S. Pat. No. 4,199,322). These experiments were conducted at a commercial textile processing facility located in South Carolina. The textile substrate was a 100% cotton (~5 oz/yd$^2$) knitted jersey material dyed olive-green in color, intended for the fabrication of military undergarments. All runs included the addition of a fabric softener (Acralube CP) at its normal use level (approximately 2%). Hydrogen peroxide (50% aqueous solution), and acetic acid (56%) were provided on-site by the textile processing facility. Zinc chloride and sodium acetate were provided by SNF, Inc. (Riceboro, Ga.). Two separate runs were performed (high and low concentration of treatment solution). The treatment compositions are described in Table 1.1. Percentage values represent the amount of feedstock added for each component. For instance, "6.32% hydrogen peroxide" means that the actual solution concentration of hydrogen peroxide is 3.16% because, as noted in the table, the feedstock is 50.00% pure.

TABLE 1.1

| | Component: | | | | | |
|---|---|---|---|---|---|---|
| | Sodium Acetate | Zinc Chloride | Hydrogen Peroxide | Acetic Acid | Acralube CP | Water |
| Purity of Feedstock | 100.00% | 100.00% | 50.00% | 56.00% | 100.00% | 100.00% |
| Run 1 (high) | 0.79% | 3.16% | 6.32% | 0.26% | 2.21% | 87.26% |
| Run 2 (low) | 0.63% | 2.11% | 4.21% | 0.00% | 2.21% | 90.84% |

Treatment solutions were prepared by adding each ingredient in order (right to left) to water. Mixtures were prepared in buckets, and poured directly into the pad trough. The pH of the solution used in Run 1 was measured to be 4.7, and the pH of the solution for Run 2 was measured to be 5.7. The fabric was treated using a horizontal pad machine, running a single strand of fabric. Settings were adjusted to obtain 95 weight % solution pickup onto the fabric for wet onto dry padding (input fabric was dry). After padding, drying was done by running the padded material through a 2-pass dryer at approximately 300° F., with speed of about 20 ypm, as per specification for the same fabric without antimicrobial finish. The dried fabric was left in a hopper overnight before compaction.

The following observations were made: Facility personnel noted that the treated textiles from both runs had acceptable softness, though not as good as when the same fabric was run without antimicrobial finish. An unpleasing acidic odor (described as "vinegary") was noted. Production staff cited the odor as being sufficiently unpleasant to preclude commercial viability for these formulations. A minor color shade change was also noted from the original fabric, which was significantly more notable after overnight storage in the hopper into which the dried fabric was placed. The appearance of the fabric was also mottled with discrete areas of significant discoloration similar to bleached spots—this may have been due to inadequately dissolved sodium acetate which reacted with the fabric during hot storage conditions piled in a hopper overnight after drying. Fabric stored for several weeks without laundering or rinsing continued to fade further in color, and continued to exude a vinegary smell. The staff of the textile processing facility stated that both the discoloration and odor issues were individually serious enough to preclude commercial production feasibility of these formulations and methods.

The material of Run 1 was subjected to multiple laundering cycles as described herein (cold water laundering, dried after every five wash cycles, Tide® detergent), and then tested for antimicrobial efficacy. The as-produced material, material that had been rinsed one time, as well as material that had been laundered for 4 cycles, as described herein, showed a (full kill) of *Staphylococcus aureus* using test methods described herein. Material of Run 1 that had been laundered for 10 cycles or 25 cycles showed a 4.7-log reduction of *Staphylococcus aureus*. Material of Run 1 that had been laundered for 50 cycles showed a 2.4-log reduction of *Staphylococcus aureus*.

The material of Run 1 was subjected to multiple laundering cycles as described herein, and then tested for antimicrobial efficacy. The as-produced material, material that had been rinsed one time, as well as material that had been laundered for either 4, 10, or 25 cycles, as described herein, showed a (full kill) of *Klebsiella pneumoniae*. Material of Run 1 that had been subjected to 50 laundering cycles showed a 0.8-log reduction of *Klebsiella pneumoniae*.

The material of Run 1 was subjected to multiple laundering cycles as described herein, and then tested for antimicrobial efficacy. The as-produced material, material that had been rinsed one time, as well as material that had been laundered for either 4, 10, or 25 cycles, as described herein, showed a (full kill) of *Escherichia coli*. Material of run 1 that had been subjected to 50 laundering cycles showed zero reduction of *Escherichia coli*.

The material of Run 2 was subjected to multiple laundering cycles as described herein, and then tested for antimicrobial efficacy. The as-produced material, material that had been rinsed one time, as well as material that had been laundered for 4 cycles, as described herein, showed a (full kill) of *Staphylococcus aureus*. Material of Run 2 that had been laundered for 10 cycles showed a 2.0-log reduction of *Staphylococcus aureus*. Material of Run 2 that had been laundered for 25 or 50 cycles showed a 0.5-log reduction of *Staphylococcus aureus*.

The material of Run 2 was subjected to multiple laundering cycles as described herein, and then tested for antimicrobial efficacy. The as-produced material, material that had been rinsed one time, as well as material that had been laundered for either 4 or 10 cycles, as described herein, showed a (full kill) of *Klebsiella pneumoniae*. Material of Run 2 that had been subjected to 25 or 50 laundering cycles showed zero reduction of *Klebsiella pneumoniae*.

The material of Run 2 was subjected to multiple laundering cycles as described herein, and then tested for antimicrobial efficacy. The as-produced material, and material that had been rinsed one time, showed a (full kill) of *Escherichia coli*. Material of Run 2 that had been subjected to as well as material that had been laundered for 4, 10, or 25 laundering cycles showed zero reduction of *Escherichia coli*.

Example 2

Pilot-Scale Antimicrobial Textile Production Using a Solution of Zinc Chloride, and Hydrogen Peroxide, with Addition of Hydroxide (No Acetate).

The materials, equipment and methods of Example 1 were followed, with the exception that the treatment solutions were of an improved composition, and other details noted below. The treatment formulation did not contain acetate or acetic acid, and the pH was adjusted to 7.5 using sodium hydroxide. The actual treatment compositions used are given in Table 2.1.

TABLE 2.1

| | Component: | | | | | |
|---|---|---|---|---|---|---|
| | Sodium Acetate | Zinc Chloride | Hydrogen Peroxide | Acetic Acid | Acralube CP | Water[1] |
| Purity of Feedstock | 100.00% | 100.00% | 50.00% | 56.00% | 100.00% | 100.00% |
| Run 3 (high conc.) | — | 1.76% | 4.71% | — | 2.47% | 91.06% |
| Run 4 (low conc.) | — | 0.88% | 2.35% | — | 2.47% | 94.29% |

[1]includes water contained in NaOH solution used for pH adjustment

The treatment formulations were prepared by adding zinc chloride into water (noting an exotherm), and adding hydrogen peroxide into the aqueous solution of zinc chloride. The pH was adjusted after HP addition, but before addition of softener. Settings were adjusted to obtain 85 weight % solution pickup onto the fabric for wet onto dry padding (input fabric was dry).

Runs 3 and 4 of the current example, and runs 1 and 2 of Example 1 were done using a Wet-on-Dry (WOD) process, wherein the material entering the treatment solution was dry. The production process utilized by most textile factories is Wet-on-Wet (WOW). This is due to economics, and efficiency of factory utilization: wet on dry processing adds an extra drying step into the production (fabrics emerge from bleaching or dyeing step wet—WOD would require an extra drying step before padding with finishing agents). The process cost for an extra drying step is estimated at $0.10/lb of fabric, at least. This cost does not consider the opportunity cost using the drying equipment while other materials could be being processed on that equipment.

A WOW run (Run 5) was performed using the composition of Table 2.2.

TABLE 2.2

| | Component: | | | | | |
|---|---|---|---|---|---|---|
| | Sodium Acetate | Zinc Chloride | Hydrogen Peroxide | Acetic Acid | Acralube CP | Water[1] |
| Purity of Feedstock | 100.00% | 100.00% | 50.00% | 56.00% | 100.00% | 100.00% |
| Run 5 (WOW) | — | 7.50% | 20.00% | — | 21.00% | 51.50% |

[1]includes water contained in NaOH solution used for pH adjustment

Again, the pH was adjusted to 7.5 using NaOH. Note that the incoming wet fabric contains a significant amount of water (i.e. 40-70%). This water dilutes the treatment formulation that is applied in the pad bath. Thus it is necessary to prepare the treatment formulation at a significantly higher concentration to enable wet on wet padding, while still targeting the same overall amount of chemical applied to the fabric. The pad bath composition pickup for the wet-on-wet process was 15%. For wet-on-wet processing, a pre-dilution process is utilized, where the pad mix is prepared at higher concentration, and mixed with water in the pad trough at the beginning, and then fed with the same higher concentration feed mix to compensate for the water being brought into the system by the wet fabric. This process compensates for the dilution of pad bath that often occurs in wet-on-wet systems. For Run 5, the solution was prepared to 10% pickup specification instead of 15%, because two buckets of mix were added with one bucket of water into the pad trough.

The following observations were made: The products from Runs 3-5 were visually indistinguishable from control fabric that had been prepared with only softener added (no antimicrobial). There was no odor noted during the processing, or from the finished fabric. A mild sheen was noted for the fabric prepared in run 5 the wet-on-wet (WOW) processing, as well as a small shade change line at a fold for that sample. Production staff originally noted that the "hand" (vernacular for the measure of softness utilized in textile industry) was inadequate on the as-dried samples. After compaction; however, the samples were reported to have acceptable hand. After padding and drying, the samples are compacted. In many cases the freshly dried samples are allowed to sit for a period of 1-3 days before compacting, which permits a moisture regain from the atmosphere step that 'relaxes' the fabric, and prevents dimensional distortion later. The compacting consists of passing the fabric through steam, following by passing through rollers that flatten the fabric, and then fold it: this folded fabric can be conveniently boxed and may be cut to shape at need in the stacked folded configuration. This process is part of normal textile production procedure.

Relative to Runs 1 and 2 (Example 1), the chemical utilization for Run 4 was reduced four-fold for $ZnCl_2$, by 100% for acetate ingredients, and by 50% for HP. Small amounts of NaOH were required as an additional ingredient. Estimated cost for chemicals was reduced by between one-half and two-thirds using the improved method and formulations of Example 2 (versus the prior art method of Example 1). Furthermore, the process was found to be commercially viable, as all of the drawbacks which were observed in Example 1 were eliminated.

The materials of Runs 3, 4, and 5 of this example were subjected to multiple laundering cycles (in cold water), as described herein, and then tested for antimicrobial efficacy. For all three runs, the as-produced samples, as well as samples that had been rinsed, or laundered either 10 or 25 cycles, as described herein, showed a greater than 5.50 log-reduction (full kill) of both *Klebsiella pneumoniae* and *Staphylococcus aureus* (tested separately). These results clearly demonstrate that the formulations and methods of the current invention give durable antimicrobial efficacy that is significantly improved over the prior art. For instance, the material of Run 4 of the current example, showed superior antimicrobial efficacy to the material of Run 2 (Comparative Example 1), despite the fact that the concentration of zinc chloride and hydrogen peroxide in Run 4 were half that used in Run 2. Furthermore, in Run 4, the use of acetate and acetic acid was eliminated.

Example 3

Pilot-Scale Antimicrobial Textile Production Using a Mixture of Zinc chloride, zinc nitrate, hydrogen peroxide, sodium hydroxide, EDTA, and Sodium Stearate.

The materials, equipment and methods of Example 1 were followed, with the exception that the treatment formulation were of an improved composition, and other details as noted below. The treatment formulation did not contain acetate or acetic acid. The actual amount of each reagent added to prepare the treatment formulation used is given in Table 3.1, and the balance of the composition was distilled water. Reagents, except for softener, were combined and then homogenized in a large commercial blender for approximately 5-10 minutes. Each blender batch of approximately 3.5 gallons was passed through a nylon mesh screen with a 200 micron pore opening, and several batches were then combined to obtain the final working volume of approximately 20 gallons of treatment formulation. The required amount of softener was then added. Wet pickup was measured to be 90 weight %. These experiments were conducted at a commercial textile processing facility located in South Carolina. The textile substrate for the Runs 6, 7, and 8 was a 100% cotton (~5 oz/yd$^2$) knitted jersey material dyed olive-green in color, intended for the fabrication of military undergarments. For Run 9, a black cotton/polyester blend material was used. All runs included the addition of a fabric softener (Acralube CP) at its normal use level. Hydrogen peroxide (50% aqueous solution), was provided on-site by the textile processing facility. Zinc chloride ("ZC", solid), and zinc nitrate ("ZN", solution, 17% zinc content) were provided by SNF, Inc. (Riceboro, Ga.). Sodium hydroxide (99%) was purchased from AAA Chemicals (Pasadena, Tex.). Sodium stearate ("NaSt", cat#269880010) was purchased from Acros Organics (New Jersey, USA). EDTA-tetrasodium salt, dihydrate (cat #03695) was purchased from Fluka. The treatment formulation of Run 6 was subsequently diluted for Runs 7, 8, and 9, as described in Table 3.1, and additional softener was added to maintain a constant softener concentration. The pH of all four treatment formulations was between 4.8 and 5.0. There was some foaming observed, but homogenization was good for the solutions as they easily passed through a 200 micron filter. There was no spotting or discoloration evident on the treated materials. After drying, a "ball burst" test was performed on the treated materials of Runs 6, 7, and 8, as well as the untreated fabric. All values were between 80 to 85 pounds, indicating no deterioration of the fabric.

TABLE 3.1

Composition of Treatment Solutions (in weight %).

| | \multicolumn{7}{c}{Component:} | | | | | | |
|---|---|---|---|---|---|---|---|
| | $ZC^1$ | $ZN^2$ | HP | NaSt | NaOH | $EDTA^3$ | Acra-CP |
| Run 6 (WOD) | 3.0% | 4.2% | 7.5% | 0.50% | 2.7% | 0.05% | 2.2% |
| Run 7 (WOD) | 2.0% | 2.8% | 5.0% | 0.33% | 1.8% | 0.03% | 2.2% |
| Run 8 (WOD) | 1.4% | 1.9% | 3.4% | 0.22% | 1.2% | 0.02% | 2.2% |
| Run 9 (WOD) | 2.1% | 1.9% | 5.3% | 0.35% | 1.9% | 0.03% | 2.2% |

Notes:
[1] as $ZnCl_2$;
[2] as $Zn(NO_3)_2$;
[3] as EDTA•4Na•$2H_2O$

Utilizing methods described herein, the treated antimicrobial textiles of Runs 6-9 were subjected to repeated in-house laboratory laundering, followed by microbiology testing to evaluate the durability of the antimicrobial treatments. Samples were laundered in HOT water using ATCC detergent, and dried after every laundering cycle. Microbiology testing was performed on samples after either 15, 20, or 25 laundering cycles using *E. coli*, as described herein. The results are shown in Table 3.2.

TABLE 3.2

Antimicrobial Efficacy Against *E. coli* After Indicated Number of Laundering Cycles.

| | Average Log Reduction | | |
|---|---|---|---|
| Sample | 15 cycles | 20 cycles | 25 cycles |
| Run 6 | 7.6* | 7.6* | 5.9 |
| Run 7 | 7.6* | 6.3 | 6.6 |
| Run 8 | 7.6* | 6.9 | 4.6 |
| Run 9 | 6.6 | 6.9 | 5.0 |

(*= "full kill")

In addition, samples of treated material from Run 6 were sent to independent certified laboratories (Precision Testing Laboratories (PTL) of Nashville, Tenn., and WUXI-AppTec laboratories of Marietta, Ga.) for evaluation of durable antimicrobial efficacy after laundering using AATCC standard methods, and for a series of physical property tests common in the textile industry. The following results were obtained:

Fabric Yarn Count (ASTM D 3887): 32 (Wales), 38 (Courses)
Colorfastness to Laundering (AATCC-61, 3A, 3 cycles): Class 4.5
Colorfastness to Crocking (AATCC 8): Class 5 (dry), Class 4.5 (wet)
Colorfastness to Light (AATCC 16, opt. A, 40 hours): Class 4.5
Bursting Strength (ASTM D 3787): 69 lbs.
Labile Sulfur (Fed Std. 191-2020): Pass
pH (AATCC 81): 6.3
Dimensional Stability, %, AATCC 135, table 1 (1, IV, Aii) 5 cycles): −11.1 (Wales), −6.3 (Courses)

Assessment of Antibacterial Finishes on Textile Materials (AATCC 100), after 25 launderings: >99.95% (SA #6538), >99.94% (KP #4352), >99.93% (EC #8739)

The treated textiles of this example were subjected to multiple laundering cycles as described herein, and then tested for antimicrobial effect after laundering against various bacteria species using methods described herein. The results are shown in the Table 3.3:

TABLE 3.3

Antimicrobial Effect After Multiple Launderings

| | Average Log Reduction of Viable Bacteria Material of Example 3: | | | | |
|---|---|---|---|---|---|
| | Run 6 | Run 6 | Run 8 | Run 8 | Run 8 |
| | \multicolumn{5}{c}{# of Launderings (Hot):} | | | | |
| ORGANISM | 25 | 50 | 25 | 50 | 75 |
| *S. aureus* | 6.89* | 6.29* | 6.89* | 6.29* | 4.20 |
| *S. epidermidis* | 4.33* | | 4.33* | | |
| MRSA | 5.49* | | 5.49* | | |
| *K. pneumoniae* | 6.15* | 6.74 | 6.15* | 6.13 | 0.99 |
| *E. coli* | 7.80* | 7.86* | 7.80* | 7.86* | 0.78 |
| *P. aeruginosa* | 6.77 | | | | |
| *Streptococcus pyogenes* | 5.19* | 4.86 | 5.19* | 4.86 | |
| VRE | 5.95* | | 5.23 | | |
| *Enterococcus faecium* | 5.94* | 5.94* | 5.94* | 5.94* | |
| *Micrococcus luteus* | 4.17 | 5.17 | 5.00 | 5.95* | |
| *Candida albicans* | 2.92 | | | | |
| *Proteus vulgaris* | 8.11* | 8.11* | 8.11* | | |

(*= Full Kill)

Example 4

Preparation of an Antimicrobial Adhesive Article

An acetate-free treatment formulation comprising metal derivative and hydrogen peroxide is prepared. For instance, any of the treatment formulations described in Tables 2.1 and 2.2 of Example 2 (above) may be used. A treatment formulation is combined with an aqueous emulsion of a polymer suitable for use in preparation of a pressure sensitive adhesive, such as the emulsions described in U.S. Pat. Nos. 4,892,905 or 5,276,084. The mixture is applied to a substrate, such as paper, or a polymer film or tape, utilizing methods known in the art, and then cured by drying in an oven. The resulting pressure-sensitive adhesive is expected to have antimicrobial properties.

Example 5

Preparation of Antimicrobial Paints and Coatings.

A acetate-free treatment formulation comprising metal derivative and hydrogen peroxide with a composition substantially similar to the treatment formulation used in Run 6, of Example 3 was prepared, except that the solution did not contain softener. The treatment formulation was mixed with several different commercially-available coating materials. All mixtures contained 10% by weight of the acetate-free treatment formulation and 90% by weight of the commercial coating material. Three commercial coating materials were used: Coronado "Aqua-Plastic" water-based urethane coating; Coronado "Seal & Finish" clear acrylic coating; and Olympic white semi-gloss "kitchen & bath" 100% acrylic latex paint. The mixtures were applied to thin Mylar sheets using a BYK coating bar (5 mil coating thickness), allowed to dry, and then stored for approximately one week. The coated samples were found to be adherent to the substrates, and appeared to cure normally. Antimicrobial efficacy was tested using ASTM method E2180-07 *"Standard Test Method for Determining the Activity of Incorporated Antimicrobial Agent(s) in Polymeric or Hydrophobic Materials"*, also known as the "Agar-Slurry" test. In overnight exposure to *S. aureus*, all three coatings gave "full kill" of the bacteria (>4 log reduction), compared to uncoated Mylar sheets.

Example 6

Comparison of Corrosion Resistance of Acetate-Free Treatment Formulation Comprising Metal Derivative and Hydrogen Peroxide.

A treatment formulation comprised of approximately 4% zinc chloride, 7% hydrogen peroxide, and approximately 75% of the full amount of sodium hydroxide that would have been required to raise the pH of the treatment solution to pH=7.5 (i.e. approximately 1.8%) was prepared, and then divided into two portions. To one portion, enough EDTA-tetrasodium salt was added to give a solution concentration of approximately 0.025% EDTA-tetrasodium salt. Approximately 10 mL of each treatment formulation were poured into separate glass petri dishes. A single steel nail was placed into each solution. After several minutes, corrosion of the nail was observed in the dish with no EDTA addition, as evidenced by significant foaming, evolution of gas and development of characteristic rust color in the solution, and on the nail. In contrast, there was only slight evidence of corrosion in the dish containing EDTA. This demonstrates the beneficial effect of EDTA on stabilizing the acetate-free treatment formulations comprising metal derivative and hydrogen peroxide against decomposition induced by contact with iron. The stabilized solutions are expected to have a significantly longer useful storage life than unstabilized solutions, and be less corrosive to equipment.

Example 7

Comparison of Corrosion Resistance of Acetate-Free Treatment Formulation Comprising Metal Derivative and Hydrogen Peroxide, as a Function of Relative Concentrations of Nitrate and Chloride Ion.

Several aqueous treatment formulations comprising various ratios of zinc nitrate and zinc chloride were prepared. In all cases, the total concentration of zinc salts was equal to approximately 4%. Each solution also contained approximately 5% hydrogen peroxide, 0.33% sodium stearate, and 1.8% sodium hydroxide. The formulations were prepared by mixing the ingredients in water using a magnetically-driven stirrer. The ratios of zinc chloride and zinc nitrate used are shown in Table 6.1. Approximately 10 ml of each solution was placed into a petri dish and a steel screw was placed into each solution. After approximately 10 minutes, visual observations were made regarding the reactivity of the solutions with the steel screw, as indicated in Table 6.1. The results clearly indicate that addition of nitrate reduces the reactivity of the acetate-free treatment formulation comprising metal derivative and hydrogen peroxide with steel, and stabilizes the treatment formulation against decomposition. The stabilized solutions are expected to have a significantly longer useful storage life than unstabilized solutions.

TABLE 7.1

Effect of Zinc Nitrate to Zinc Chloride Ratio on Corrosion of Steel.

| ZC/ZN (wt %) | Observations |
| --- | --- |
| 100/0 | Foaming, Extensive formation of rust-colored precipitate |
| 90/10 | Foaming, Extensive formation of rust-colored precipitate |
| 75/25 | Foaming, Moderate formation of rust-colored precipitate |
| 50/50 | Foaming, Slight formation of dark precipitate |
| 0/100 | Slight foaming, No discoloration |

Example 8

Effect of Homogenization on Appearance of Textiles Treated Using Acetate-Free Treatment Formulations Comprising Metal Derivative And Hydrogen Peroxide.

An aqueous treatment formulation comprising essentially 4% zinc chloride, 5% hydrogen peroxide, 0.33% sodium stearate, and 1.8% sodium hydroxide was prepared by mixing the ingredients in water using a magnetically-driven stirrer. This was used to treat a 100% cotton (~5 oz/yd$^2$) knitted jersey material dyed olive-green in color, by immersing the fabric in the formulation, and then passing the fabric through a set of had-driven rollers to expel excess liquid so that the wet pickup of treatment formulation (relative to dry fabric) was approximately 115 weight percent. The fabric was dried in an oven at 80° C. for 30 minutes. There was a conspicuous presence of discoloration by deposits of white residue imbedded in, and adhering to, the surface of the surface of the treated fabric. The experiment was repeated using an identical formulation which had been passed through a plastic mesh screen with a pore opening size of approximately 200 microns. Passage of the formulation, which contained suspended white gelatinous material, through the screen was assisted by pressing and scraping the screen with a rubber spatula. The white discoloration of the dried fabric was noticeably reduced, and the appearance was significantly improved. The experiment was repeated again, using an identical treatment formulation that had been homogenized in an ordinary kitchen blender for one minute. This treatment formulation passed through the screen easily without the aid of a spatula. Fabric treated with this homogenized formulation showed no visible white deposits or discoloration after drying. Storage of the homogenized treatment formulation for several days resulted in some settling of white precipitate to the bottom of the storage container; however, this was easily redispersed with gentle agitation. The redispersed suspension easily passed through the screen and was used to treat fabric. The resulting material showed no visible white deposits or discoloration after drying.

Example 9

Effect of Substituting Chloride Ion by Nitrate Ion on the Processability of Acetate-Free Treatment Formulation Comprising Metal Derivative and Hydrogen Peroxide.

An aqueous treatment formulation comprising essentially 4% zinc chloride, 5% hydrogen peroxide, 0.33% sodium stearate, and 1.8% sodium hydroxide (equal to approximately 75% of the amount that would have been required to raise the pH of the solution to 7.5) was prepared by mixing the ingredients in water using a magnetically-driven stirrer. This formulation was homogenized in an ordinary kitchen blender so that it would pass through a mesh of approximately 200 micron pore size. A second aqueous treatment formulation comprising essentially 4% zinc nitrate, 5% hydrogen peroxide, 0.33% sodium stearate, and 1.8% sodium hydroxide was prepared by mixing the ingredients in water using a magnetically-driven stirrer. An attempt to homogenize this formulation using an ordinary kitchen blender resulted in the formation of a thick gel-like emulsion which was impossible to filter through a mesh of approximately 200 micron pore size. Thus, it is demonstrated that presence of some chloride ion is preferred when zinc nitrate is used in the practice of this invention. In other words, a combination of both chloride and nitrate is preferable to either one alone.

Example 10

Effect of the Addition of Long Chain Fatty Acids on Durable Antimicrobial Activity.

Antimicrobial textiles were prepared using acetate-free treatment formulation of this invention comprising metal derivative and hydrogen peroxide, according to methods and formulations described herein. The antimicrobial textiles were tested for retention of antimicrobial efficacy after laundering for various numbers of cycles, using methods described herein. It was found that addition of approximately 0.25 to 0.50% of a fatty acid, or a fatty acid salt to the acetate-free treatment formulation improved retention of antimicrobial properties of the treated textiles after laundering; and, that longer chain fatty acids gave the most improvement. For instance, sodium stearate (C18) was more effective than sodium laurate (C12) or sodium octoate (C8).

Example 11

Use of a Acetate-Free Treatment Formulation Comprising Metal Derivative and Hydrogen Peroxide in the Manufacture of an Antimicrobial Wound Dressing.

A treatment formulation comprising approximately 2% zinc chloride, 3% hydrogen peroxide, and approximately 1% sodium hydroxide is homogenized in a blender and filtered through a 200 micron screen. This formulation is used to saturate an absorbent substrate such as woven cotton gauze or nonwoven rayon felt material. The wet absorbent substrate is pressed to remove excess liquid. The damp substrate is then dried. The dried substrate may be used directly as an antimicrobial wound dressing, or optionally washed in distilled water until the conductivity of the distilled water falls to a predetermined level which denotes the absence of further leachable material, and then re-dried. The redried material may be used directly as a wound dressing, or optionally subjected to tests for antimicrobial activity, and biocompatibility. The results of these tests can be used to select a modified concentration of components in subsequent treatment formulations in order to optimize the results of antimicrobial efficacy and biocompatibility of subsequent samples until a useful and desirable balance of properties has been achieved. The treatment formulation may also optionally comprise zinc nitrate, EDTA, or a binding agent.

Example 12

Use of a Acetate-Free Treatment Formulation Comprising Metal Derivative and Hydrogen Peroxide in the Manufacture of Antimicrobial Animal Litter or Bedding Material.

A treatment formulation substantially similar to that used in Example 3, Run 6 was prepared. Fifty grams of ordinary clay cat litter was added to approximately 250 grams of treatment formulation. The mixture was shaken briefly, then allowed to sit for approximately two minutes, and then the liquid was decanted. The damp litter was allowed to air dry. The process was repeated using treatment formulation which had been diluted with two volumes of water (to 33% of the original concentration). Both samples of dried litter were tested for antimicrobial activity by placing 1 gram of litter in a culture tube, and then adding 1.5 mL of bacterial suspension (~$10^5$ cfu/mL) to each litter sample. The tubes were stored overnight at 37° C. before being extracted with 20 mL of Letheen broth and enumerated using standard microbiology techniques. Log reductions for both $E.\ coli$ (EC) and $S.\ aureus$ (SA) were calculated based on comparison to untreated cat litter. The results are presented in Table 12.1, and indicate very good antimicrobial efficacy for the materials. It is expected that antimicrobial animal litter or bedding will provide odor reduction, and reduce the spread of germs. This material may also be used for the absorption of spills, particularly for spills containing biological material like blood, urine, food, and the like.

TABLE 12.1

| Efficacy of Antimicrobial Cat Litter | | |
|---|---|---|
| Sample | SA | EC |
| Full Strength | 5.69* | 6.69* |
| Diluted (33%) | 5.69* | 6.69* |

*indicates full kill

Example 13

Demonstration of Resistance of Antimicrobial Textiles to Discoloration.

A treatment formulation substantially similar to that used in Example 3, run 6 was prepared. The formulation was padded onto two different white textile substrate materials: a woven 100% polyester fabric of approximately 5 oz/yd$^2$, and a woven 100% cotton fabric of approximately 4 oz/yd$^2$. Discoloration was tested by an adaptation of AATCC method 151, which is meant to measure the susceptibility of a textile for soil redeposition in laundering (ostensibly meant to simulate 100 'normal' cycles). It was found that the samples tested by this method were virtually indistinguishable from control samples (untreated) used for reference. This test is important because one of the major drawbacks of many antimicrobial textile treatments based on cationic biocides (most common type utilized) is that they are highly susceptible to discoloration by this method—particularly because the method uses high clay content dirt to simulate laundering soil, and the negatively charged clay colloids readily bind to cationic surface sites. To substantiate this effect, locally-purchased antimicrobial t-shirts (JC Penney Stafford Ease (60% cotton, 40% polyester) and Stafford Heavyweight (100% cotton)) treated with Aegis microbicide were assessed by the same method, and showed higher discoloration than the materials of the current invention.

Example 14

Demonstration of Biocompatibility of Antimicrobial Textiles.

A green cotton knit substrate (as described in Example 3) was substrate treated according to the compositions and methods of this invention, using conditions and compositions substantially similar to that described in Example 3, Run 8. Samples of the treated substrate were rinsed with water, or laundered according to procedures described herein, then tested according to the ISO 10993-5 and ASTM F895-84 "Standard test method for agar diffusion cell culture screening for cytotoxicity" guidelines. The test requires positioning test articles onto the agar overlay protecting cellular monolayer from mechanical damage; and evaluating the changes in cells condition after 24 and 48 hours. This test is intended for qualitative assessment of cytotoxicity potential of the substrates by detecting and describing the zones of cellular changes extending beyond the perimeter of the specimen of material. The zones are visualized by means of vital neutral red dye. The tested samples were found to give scores of 2 or lower, indicating that the samples are biocompatible and non-cytotoxic.

Example 15

An Acetate-Free and Peroxide-Free Aqueous Binder Composition for Hydrogen Peroxide that May be Used for Treating a Substrate and Imparting Durable Antimicrobial Activity to Said Substrate, Comprising a Metal Derivative, and a Source of Hydroxide Ion.

An aqueous acetate-free and peroxide-free binder composition is prepared according to the teachings of this invention. For example, a mixture which has essentially the following composition: 3.0% zinc chloride, 4.2% zinc nitrate, 2.7% sodium hydroxide and 0.05% EDTA, and 89.55% water. This mixture is prepared by dispersing the required amount of each ingredient in a known volume of water, and then mixing and homogenizing (in a blender, for example), until it is able to easily and completely pass through a mesh filter having a 200 micron pore size, in order to give an acetate-free and peroxide-free aqueous binder composition comprising a metal derivative, and a source of hydroxide ion. This binder may be used for treating a substrate and imparting durable antimicrobial activity to said substrate after adding hydrogen peroxide to the binder. This binder composition can be stored until it is mixed with enough hydrogen peroxide to give a hydrogen peroxide concentration of approximately 2% to 7% (or as otherwise specified in the preferred embodiments) in the treatment solution. The mixture of binder composition and hydrogen peroxide can be used to treat a substrate in order to impart antimicrobial properties to the substrate. The binder composition or the mixture of binder solution and hydrogen peroxide may be diluted with water or other aqueous solutions prior to use. A concentrated form of said binder composition may be manufactured by repeating the described procedure while appropriately reducing the "known volume of water" cited above in order to increase the concentration of all ingredients by the desired concentration factor (such as 2x, 3x, 4x, or higher). Said concentrated binder composition is mixed with the required (or desired) amount of hydrogen peroxide and then diluted with water or other aqueous solutions prior to use as a treatment formulation for imparting antimicrobial properties to a substrate. Said binder composition may also be applied to a substrate without further addition of hydrogen peroxide using methods described herein for the application of peroxide-containing compositions. The treated substrate (dried or undried) may subsequently be exposed to sufficient hydrogen peroxide to give the treated substrate durable antimicrobial properties.

Example 16

An Acetate-Free and Peroxide-Free Aqueous Binder Composition for Hydrogen Peroxide that May be Used for Treating a Substrate and Imparting Durable Antimicrobial Activity to Said Substrate, Comprising a Metal Derivative, Source of Hydroxide Ion, and a Durability-Enhancing Agent.

An acetate-free and peroxide-free binder composition having a formulation similar to that given in Example 15 was prepared. Various durability-enhancing agents (DEAs) were selected according to the methods of this invention and added to said binder composition (prior to homogenization) as described in Table 16.1.

TABLE 16.1

Formulations with Durability-enhancing Agents (DEA)

| Formulation | DEA | Concentration of DEA |
|---|---|---|
| 16A | None | |
| 16B | Sodium Stearate | 0.5% |
| 16C | PEI[a] | 0.5% |
| 16D | AL-CP[b] | 2% |
| 16E | AL-CG[c] | 0.5% |
| 16F | AL-CG + PEI | 2% + 0.5% |

[a]PEI = poly(ethyleneimine), Lupasol G20 (BASF)
[b]AL-CP = Acralube CP softener (Peach State Labs)
[c]AL-CG = Acralubs CG softener (Peach State Labs)

For formulation 16F, both AL-CG (2%) and PEI (0.5%) were added. Binders were then mixed with approximately 3% HP, and used to treat cotton textile material according to methods described herein. Treated materials were laundered repeatedly according to methods described herein, and then tested for antimicrobial efficacy according to methods described herein. In all cases, the formulations that contained DEA were found to give more durable antimicrobial efficacy than the formulation without DEA. In other words, addition of DEA allowed the finished textiles to retain antimicrobial efficacy for a greater number of laundering cycles.

Example 17

Demonstration of Regenerable Antimicrobial Efficacy of a Treated Substrate.

A substrate, such as a cotton textile is treated with an acetate-free treatment formulation as described in Example 3, and the antimicrobial efficacy is measured as described herein. The treated substrate is then used in its intended normal application and/or washed, rinsed, aged, or stored, until a subsequent measurement of antimicrobial efficacy indicates that a full or partial loss of efficacy has occurred. The treated substrate is then "regenerated" by exposure to an aqueous source of hydrogen peroxide, that may be an actual solution of hydrogen peroxide, or a compound which forms salts or additive compounds with hydrogen peroxide; included among these are sodium perborate, sodium carbonate peroxide, sodium peroxyphosphate, urea peroxide, potassium persulfate, and others; which, when added to water, hydrolyze into hydrogen peroxide. The treated substrate is then dried, and the antimicrobial efficacy is measured. If the antimicrobial efficacy has been restored, then the treated substrate can be used as an antimicrobial article with durable antimicrobial efficacy, until it is found that further recharging does not increase the antimicrobial efficacy further.

Example 18

Lab-Scale Antimicrobial Textile Production Using a Mixture of Zinc Chloride, Zinc Nitrate, Hydrogen Peroxide, Sodium Hydroxide, EDTA, And Sodium Stearate: Effect of Overall Solution Concentration on Durability of Antimicrobial Effect.

Antimicrobial cotton textile material was prepared according to the methods described in Example 3. The treatment formulation was substantially similar to that of Run 6 (Table 3.1). This sample was designated as "100%". Additional samples were prepared using treatment formulations that were diluted with water to obtain treatment formulations having concentrations of 75%, 50%, 30%, 20%, and 10% of that used to produce the 100% sample. All samples were sent to a commercial laboratory for repeated laundering in hot water (120° F.) according to AATCC standard methods. Laundered samples were tested for antimicrobial efficacy using methods described herein. It was found that all samples, except the 10% sample, retained full efficacy (>6 log reduction "full kill" against *K pneumoniae*) after 25 hot water laundering cycles. The 10% sample lost efficacy after 25 launderings, giving only a 0.7 log reduction.

Example 19

Treatment of an Elastic Bandage with Diluted Acetate-Free Treatment Formulations and Demonstration of Antimicrobial Efficacy.

Elastic bandages (compression type bandages, commonly referred to as "Ace" bandages) were treated by immersing in treatment formulations having essentially the compositions described in Table 19.1. The elastic bandages had the following approximate composition (10% polyester, 20% Spandex, and 70% cotton). In all cases, sufficient sodium hydroxide was added to neutralize the solutions to approximately 80% of the degree of neutralization that would be required to bring the pH of the solutions to 7.5. Excess treatment formulation was removed by passing the wet samples through nip rollers, and the damp bandages were dried in an oven at 80° C. The dried samples were tested for antimicrobial efficacy using methods described herein. In all cases the antimicrobial bandages were found to give a >8-log(full kill) reduction of *K pneumoniae*.

TABLE 19.1

Compositions of Treatment Formulations (balance = water)

| Sample ID | EDTA | Zinc Nitrate | Zinc Chloride | Hydrogen Peroxide | Sodium Stearate |
|---|---|---|---|---|---|
| El101 | 0.05% | 0.7% | 0.50% | 1.40% | 0.00% |
| El102 | 0.03% | 0.35% | 0.25% | 0.70% | 0.05% |
| El103 | 0.03% | 0.35% | 0.25% | 0.70% | 0.00% |
| El104 | 0.01% | 0.2% | 0.13% | 0.35% | 0.00% |
| El105 | 0.01% | 0.1% | 0.06% | 0.18% | 0.00% |

Example 20

Manufacture of Pressure-Treated Lumber.

A treatment solution substantially similar in composition to that used in Example 3 (Run #6) was prepared. This solution was diluted by mixing one part of the solution with two parts of water (i.e. 33% concentration). Twenty wooden (pine) stakes, approximately 0.5"×1.25"×18" in size (total dry weight of 2,283 grams), were placed into a metal chamber which was then sealed and evacuated using a vacuum pump. Thirteen liters (13 L) of the 33% solution was introduced into the evacuated chamber, and the chamber was then pressurized to 50 psi using argon gas, and left to sit for one hour. The chamber was opened, the stakes were removed, excess liquid was wiped off the surface of the wood, the damp stakes were weighed (4,140 g) and then allowed to air-dry for several days. The process was repeated on a second set of pine stakes using a more diluted version of the treatment solution (16.5%). After drying, ten samples from each set of stakes, along with ten untreated (control) stakes were imbedded into the ground in a shady wooded area of Gainesville, Fla. so that approximately half the length of the stakes were buried and in direct contact with the soil. After approximately 7.5 months, the stakes were checked for damage due to fungi and insects. The stakes exposed to the treatment solutions described above exhibited considerably less damage than the untreated stakes. The stakes were returned to the ground for further evaluation at a future date. The usefulness of the present invention for pressure-treating of wood for the purpose of preservation against decay by fungi and insects is thus demonstrated.

Example 21

Demonstration of Anti-Viral Efficacy of Treated Textiles.

The antimicrobial material produced in Example 3 (Run #6) was tested for anti-viral effect as follows:

Influenza A (H1N1; ATCC VR-1469) virus was propagated and enumerated as Most Probable Numbers (MPN) using Madin-Darby Canine Kidney type I (MDCK) cell monolayers (ATCC CCL-34) as the host. Cells were grown in 6 well cell culture plates.

For enumeration, aliquots of a sample containing the virus were inoculated on freshly prepared monolayers of MDCK monolayers. The cells were then incubated in dMEM (MediaTech, USA) media containing trypsin at 35° C. and 5% CO2 for 5-7 days. Cells were monitored routinely microscopically for signs of degeneration. Cells in wells demonstrating signs of infectivity (Cytopathic effects; CPE) are recorded as positive (+) and ones that do not demonstrate any CPE are recorded as negative (−). The most probable number of infectious virus in a sample was then calculated using MPNCALC software (version 0.0.0.23). For Challenge experiments, frozen viral stock (typically 2×106 iu/ml) was thawed rapidly in a 35° C. water bath on the day of experiment. Stock was then diluted 1/100 in Phosphate Buffered Saline (PBS) supplemented with 2% Bovine Serum Albumin (BSA).

The protocol used is comparable to ASTM E 1053-97 (Standard Test Method for Efficacy of Virucidal Agents Intended for Inanimate Surfaces). Material was cut into 1" square sections. Each section was placed into a sterile Petri dish. Triplicate samples of each material were analyzed. One hundred microliters of the virus dilution described above was evenly applied to the surface of each of the test samples. The inoculums were then allowed to incubate for 120 minutes at 25° C. Each of the materials was then transferred to a sterile 50 ml conical bottom centrifuge tube (Fisher scientific, PA). To each tube 25 ml sterile Difco Letheen Broth (Becton Dickinson #263010, MD) was added. A tube containing 25 ml Letheen Broth and 0.1 ml of the diluted virus inoculum described above served as the positive control (initial). Tubes were then placed onto an orbital shaker and agitated at low speed for 15 minutes. After agitation, 5 ml of liquid from each of the tubes was removed and added to a sterile 15 ml conical bottom centrifuge tube (Fisher Scientific, PA). Ten fold dilutions of the viral suspensions were performed in PBS. The number of viable (infectious) Influenza A in each of the tubes was enumerated by the MPN procedure described above using Madin-Darby Canine Kidney type I (MDCK) cell monolayers (ATCC CCL-34). All analysis was conducted in triplicates. The viral MPN from the positive control tube was used to obtain initial challenge concentration and calculate the resulting percent reduction. The overall calculated percent reduction was 78%.

Example 22

Demonstration of Resistance of Antimicrobial Fabric to Growth of Mold.

Several antimicrobial textiles were prepared according to the materials and methods of the current invention, including those made by treating white cotton knit material in the laboratory using treatment solution and methods substantially similar to those described for Example 3 (Run #6). The antimicrobial textile was tested according to AATCC Method 30, "Antifungal Activity, Assessment on Textile Materials: Mildew and Rot Resistance of Textile Materials". This method consists of placing a fabric swatch onto a growth plate that has been seeded with a mold or fungus. Test organisms were *Aspergillus niger*, and *Cladosporium*. After seven (7) days, samples were visually evaluated for the growth of mold on the surface of the textiles. Treated textiles prepared in according to the methods of this invention exhibited substantially less growth than untreated (control) textiles.

Standard Testing and Analysis Methods Used to Evaluate the Properties of Treated Articles Described Herein:

A: Laboratory Laundering Method:

The laundering method is based on an AATCC standard method. Samples were laundered in a standard size home washing machine (for instance, Sears® Kenmore® Heavy Duty Washer) using the following settings: Water Level=LOW; Water Temperature=COLD (approximately 20° C.); Cycle Setting=NORMAL (6 minute wash). Forty (40) mL of TIDE® liquid detergent for front-end loaders was used for each wash cycle. Ten sheets of ballast fabric (100% white cotton Gerber® diapers each weighing approximately 35 grams each) were added to each wash load. The washer was started and allowed to fill, and then detergent was added, followed by the textile samples and ballast. After every five wash cycles, the samples were removed and placed in a standard home clothes dryer (Whirlpool® Heavy Duty Dryer) along with two sheets of ballast and dried on the high heat setting for twenty minutes. Samples for antimicrobial efficacy testing were cut from the textile samples after a specified number of laundering cycles, and the remainder of the textile sample was subjected to further laundering cycles, as needed.

Variations on the standard laboratory laundering method given above were used in some cases and include: optional rinsing of samples prior to the initial laundering cycle; use of AATCC standard detergent in place of Tide; use of the HOT temperature setting (120° F.); and, drying after every wash cycle rather than after every five cycles.

B: Microbiological Method to Verify the Antimicrobial Property of Treated Textile Materials:

Antimicrobial activity of materials prepared using the various methods and embodiments of this invention were assayed using a modified version of the American Association of Textile Chemists and Colorists (AATCC) Test Method 100 ("*Antibacterial Finishes on Textiles: Assessment of*"), a test designed to test antibacterial finishes of textile materials. Overnight cultures (ONC) of test microorganisms were generated in appropriate culture medium using standard methods. Using the ONC, an inoculum solution was prepared containing the test microorganism diluted to approximately $10^6$ CFU/ml in phosphate buffered saline (PBS). Treated substrate materials (samples) and untreated substrate control materials (controls) were cut into 2.5 cm squares and autoclaved at 121° C. for 30 minutes to eliminate pre-existing microbial contamination. After autoclaving, samples and controls (identical base textile substrate that was not subjected to an antimicrobial treatment) were allowed to cool for 15 minutes at room temperature. Samples and controls were analyzed as stacks of three layers of one-inch squares of textile material. Samples and controls were each inoculated with 500 µL of inoculum. Inoculated samples were incubated at 37° C. in sterile covered petri dishes. After 18 to 24 hours incubation, the samples and were harvested with sterile forceps, placed into separate 15 mL tubes containing 15 mL PBS, and vortexed for 30 seconds to suspend any remaining viable microorganisms into solution. Appropriate tenfold dilutions of these suspensions were made using PBS solution and spread onto bacteria culture plates containing growth medium appropriate for the desired organisms, and then incubated overnight at 37° C. After overnight culture, colonies growing on each plate were enumerated to determine antimicrobial efficacy. Data are reported as % killed or log reduction as compared to untreated controls inoculated with the same bacterial load. It is convenient to express the efficacy of a particular formulation against a particular bacterial species as "log kill", "log reduction", or simply "LR". In the following discussions, a complete kill (i.e. 100% reduction of viable bacteria) will be noted, or indicated by using an asterisk after the LR number (6.0*, for example). The individual values of LR for each replicate of a given sample are calculated relative to the average colony count for the untreated (negative) control samples. The individual LR values for that sample are then averaged, and the average LR is reported as the result. In the case where the bacterial populations of the control samples is determined immediately after inoculation, the result is reported as "t=0". In the case where control populations are determined after an incubation time identical to that of the sample being tested, the results are reported as "t=x", where x is equal to the incubation time used for the test sample (generally overnight, i.e. 18-24 hours). Unless stated otherwise, all LR values reported herein refer to t=overnight measurements. Note that t=0 LR values are generally less than t=overnight values because the bacterial populations on the untreated controls tend to increase over time. The t=0 values may be considered to reflect bactericidal values; whereas, the t=overnight values may be considered to reflect a combination of bactericidal and bacteriostatic effects. The dilution, spreading, plating and enumeration were conducted using standard microbiological techniques. The following species and strains of bacteria were used in this testing:

| | |
|---|---|
| *Staphylococcuc aureus* (SA) | ATTC 6538 |
| *Eschericia coli* (EC) | ATTC 15597 |
| *Klebsiella pneumoniae* (KP) | ATTC 13883 |

The invention claimed is:

1. A process of preparing an antimicrobial article comprising the steps of (a) providing an aqueous mixture consisting essentially of (1) hydrogen peroxide and (2) one or more chloride, bromide, nitrate, or sulfate salts of magnesium, zinc, or zirconium, (b) adding a source of hydroxide ion to the aqueous mixture to produce an antimicrobial treatment formulation having a degree of neutralization of about 50 to 100%, (c) applying said antimicrobial treatment formulation of step (b) to an article, and then (d) drying the article, wherein the molar ratio of hydrogen peroxide to said one or more chloride, bromide, nitrate, or sulfate salts of magnesium, zinc, or zirconium in the aqueous mixture is equal to or greater than 1:1, wherein an acetate-free complex of magnesium, zinc, or zirconium derivatives comprising a mixture of a hydroxide and an peroxide is incorporated into said article, and whereby durable antimicrobial activity is imparted to said article.

2. The process of claim 1, wherein the weight concentration of the metal of said salts of magnesium, zinc, or zirconium in said treatment formulation is between 0.05% and 3.0%.

3. The process of claim 1, wherein said salts of step (a) are one or more chloride, bromide, nitrate, or sulfate salts of zinc.

4. The process of claim 1, wherein said treatment formulation further comprises at least 0.1 wt % of a durability-enhancing agent selected from the group consisting of polymeric amines, long-chain fatty acids, long-chain fatty acid salts, softeners, and lubricants.

5. The process of claim 4, wherein said durability-enhancing agent is the long-chain fatty-acid salt, sodium stearate.

6. The process of claim 4, wherein said durability-enhancing agent is poly(ethyleneimine).

7. The process of claim 1, wherein said treatment formulation further comprises at least 0.01 weight percent of ethylenediaminetetraacetic acid (EDTA) or a salt thereof to stabilize said antimicrobial treatment formulation.

8. The process of claim 1, wherein (1) said article is selected from the group consisting of polymers, films, fibers, tapes, and woven, knitted, and non-woven textiles, or (2) said article comprises all or part of a wound dressing, a burn dressing, a sanitary pad, an incontinence pad, a tampon, an intrinsically antimicrobial absorbent dressing, a diaper, toilet paper, a sanitary wipe, a sponge, a cotton swab, a surgical gown, an isolation gown, a lab coat, a glove, surgical scrubs, a head cover, a hair cover, a face mask, a suture, a floor mat, a lamp handle cover, an exam table cover, a cast liner, a splint liner, padding, gauze, packaging materials, a mattress cover, bedding, a sheet, a towel, clothing, underwear, a sock, shoe-cover, an automobile air filter, an airplane air filter, an HVAC system air filter, a protective garment for military or other use, an apparatus for protection against a biohazard or biological warfare agent, food packaging material, meat packaging material, fish packaging material, apparel for food handling, a surface for food preparation, carpet, wood, lumber, paper, or paper currency.

9. The process of claim 1, further comprising a step of homogenizing the antimicrobial treatment formulation before applying it to the article in step (c).

10. A process for preparing an antimicrobial article comprising the steps of (a) providing an aqueous binder composition as produced by homogenizing an aqueous mixture of a source of hydroxide ion and one or more chloride, bromide, nitrate, or sulfate salts of magnesium, zinc, or zirconium, (b) adding sufficient aqueous hydrogen peroxide to the homonogenized aqueous mixture of step (a) to produce a treatment formulation wherein the molar ratio of hydrogen peroxide to said one or more chloride, bromide, nitrate, or sulfate salts of magnesium, zinc, or zirconium is equal to or greater than 1:1, then (c) applying said treatment formulation of step (b) to an article, and (d) drying the article which has been treated with said antimicrobial treatment formulation, wherein an acetate-free complex of magnesium, zinc, or zirconium derivatives comprising a mixture of a hydroxide and a peroxide is incorporated into said article, and whereby durable antimicrobial activity is imparted to said article.

11. The process of claim 10, further comprising, after step (c) and before step (d), the step of removing any excess of said antimicrobial treatment formulation from said article by rolling, nipping, padding, centrifuging, wringing, or blotting.

12. The process of claim 10, which further comprises the step of homogenizing the antimicrobial treatment formulation before applying the treatment formulation to the article in step (c).

13. The process of claim 10, wherein the weight concentration of the metal of said salts of magnesium, zinc, or zirconium derivatives in said treatment formulation is between 0.05% and 3.0%.

14. The process of claim 10, wherein said salts of step (a) are one or more chloride, bromide, nitrate, or sulfate salts of zinc.

15. The process of claim 10, wherein said treatment formulation further comprises at least 0.1 wt % of a durability-enhancing agent selected from the group consisting of polymeric amines, long-chain fatty acids, long-chain fatty acid salts, softeners, and lubricants.

16. The process of claim 15, wherein said durability-enhancing agent is the polymeric amine, poly(ethyleneimine).

17. The process of claim 10, wherein said treatment formulation further comprises at least 0.01 wt % of ethylenediaminetetraacetic acid (EDTA), or a salt thereof to stabilize said treatment formulation.

18. The process of claim 10, wherein (1) said article is selected from the group consisting of polymers, films, fibers, tapes, and woven, knitted, and non-woven textiles, or (2) said article comprises all or part of a wound dressing, a burn dressing, a sanitary pad, an incontinence pad, a tampon, an intrinsically antimicrobial absorbent dressing, a diaper, toilet paper, a sanitary wipe, a sponge, a cotton swab, a surgical gown, an isolation gown, a lab coat, a glove, surgical scrubs, a head cover, a hair cover, a face mask, a suture, a floor mat, a lamp handle cover, an exam table cover, a cast liner, a splint liner, padding, gauze, packaging materials, a mattress cover, bedding, a sheet, a towel, clothing, underwear, a sock, shoe-cover, an automobile air filter, an airplane air filter, an HVAC system air filter, a protective garment for military or other use, an apparatus for protection against a biohazard or biological warfare agent, food packaging material, meat packaging material, fish packaging material, apparel for food handling, a surface for food preparation, carpet, wood, lumber, paper, or paper currency.

19. A process for preparing an antimicrobial article comprising the steps of (a) providing an aqueous binder composition as produced by homogenizing an aqueous mixture of a source of hydroxide ion and one or more chloride, bromide, nitrate, or sulfate salts of magnesium, zinc, or zirconium, (b) applying the homogenized aqueous mixture of step (a) to an article, then (c) exposing said article to aqueous hydrogen peroxide, and (d) drying said article which has been treated with said binder composition and aqueous hydrogen peroxide, wherein an acetate-free complex of magnesium, zinc, or zirconium derivatives comprising a mixture of a hydroxide and a peroxide is incorporated into said article, and whereby durable antimicrobial activity is imparted to said article.

20. The process of claim 19, further comprising, after step (c) and before step (d), the step of removing excess aqueous binder composition and aqueous hydrogen peroxide from said article.

21. The process of claim 19, further comprising, after step (b) and before step (c), a drying step.

22. The process of claim 19, wherein the weight concentration of said metal of said salts of magnesium, zinc, or zirconium derivatives in said aqueous binder composition is between 0.05% and 3.0%.

23. The process of claim 19, wherein said salts of step (a) are one or more chloride, bromide, nitrate, or sulfate salts of zinc.

24. The process of claim 19, wherein said aqueous binder composition further comprises at least 0.1 wt % of a durability-enhancing agent selected from the group consisting of polymeric amines, long-chain fatty acids, long-chain fatty acid salts, softeners, and lubricants.

25. The process of claim 24, wherein said durability-enhancing agent is the long-chain fatty-acid salt, sodium stearate.

26. The process of claim 24, wherein said durability-enhancing agent is the polymeric amine, poly(ethyleneimine).

27. The process of claim 19, wherein said aqueous binder composition further comprises at least 0.01 wt % of ethylenediaminetetraacetic acid (EDTA), or a salt thereof to stabilize said binder composition.

28. The process of claim 19, wherein
(1) said article is selected from the group consisting of polymers, films, fibers, tapes, and woven, knitted, and non-woven textiles, or
(2) said article comprises all or part of a wound dressing, a burn dressing, a sanitary pad, an incontinence pad, a tampon, an intrinsically antimicrobial absorbent dressing, a diaper, toilet paper, a sanitary wipe, a sponge, a cotton swab, a surgical gown, an isolation gown, a lab coat, a glove, surgical scrubs, a head cover, a hair cover, a face mask, a suture, a floor mat, a lamp handle cover, an exam table cover, a cast liner, a splint liner, padding, gauze, packaging materials, a mattress cover, bedding, a sheet, a towel, clothing, underwear, a sock, shoe-cover, an automobile air filter, an airplane air filter, an HVAC system air filter, a protective garment for military or other use, an apparatus for protection against a biohazard or biological warfare agent, food packaging material, meat packaging material, fish packaging material, apparel for food handling, a surface for food preparation, carpet, wood, lumber, paper, or paper currency.

29. The process of claim 1, wherein said article is selected from the group consisting of polymers, films, fibers, tapes, and woven, knitted, and non-woven textiles; and wherein said durable antimicrobial activity remains effective after at least 10 laundering cycles.

30. The process of claim 10, wherein said article is selected from the group consisting of polymers, films, fibers, tapes, and woven, knitted, and non-woven textiles; and wherein said durable antimicrobial activity remains effective after at least 10 laundering cycles.

31. The process of claim 19, wherein said article is selected from the group consisting of polymers, films, fibers, tapes, and woven, knitted, and non-woven textiles; and wherein said durable antimicrobial activity remains effective after at least 10 laundering cycles.

* * * * *